United States Patent
Robertson et al.

(10) Patent No.: US 9,669,197 B2
(45) Date of Patent: Jun. 6, 2017

(54) EXPANDABLE MEMBER DISSECTION PORT AND RELATED METHODS

(71) Applicant: Boston Scientific Scimed, Inc., Maple Grove, MN (US)

(72) Inventors: David W. Robertson, Framingham, MA (US); Charles Hanes, Mobile, AL (US); Peter Lotze, Missouri City, TX (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 644 days.

(21) Appl. No.: 14/078,752

(22) Filed: Nov. 13, 2013

(65) Prior Publication Data
US 2014/0135809 A1  May 15, 2014

Related U.S. Application Data

(60) Provisional application No. 61/726,992, filed on Nov. 15, 2012.

(51) Int. Cl.
| | | |
|---|---|---|
| *A61M 29/00* | (2006.01) | |
| *A61M 29/02* | (2006.01) | |
| *A61B 17/34* | (2006.01) | |
| *A61B 17/32* | (2006.01) | |
| *A61B 17/22* | (2006.01) | |

(52) U.S. Cl.
CPC ..... *A61M 29/02* (2013.01); *A61B 17/320016* (2013.01); *A61B 17/3421* (2013.01); *A61B 2017/22061* (2013.01); *A61B 2017/320048* (2013.01)

(58) Field of Classification Search
CPC ......... A61F 2/958; A61F 2/856; A61M 25/10; A61M 25/1011; A61M 2025/0681; A61M 2025/1047; A61B 17/3421; A61B 2017/320048; A61B 17/320016; A61B 2017/00278; A61B 2017/22061; A61B 2017/3445; A61B 2017/3447; A61B 2017/3456; A61B 2017/3486
USPC ...... 604/96.01; 606/108, 159, 191, 194, 198
See application file for complete search history.

(56) References Cited

U.S. PATENT DOCUMENTS

| | | | | |
|---|---|---|---|---|
| 5,807,329 A | * | 9/1998 | Gelman | ............ A61M 25/0026 604/102.02 |
| 6,142,993 A | * | 11/2000 | Whayne | ............ A61B 18/1492 600/374 |
| 6,287,291 B1 | * | 9/2001 | Bigus | ............ A61F 2/958 604/523 |

(Continued)

*Primary Examiner* — Katherine M Shi
(74) *Attorney, Agent, or Firm* — Brake Hughes Bellermann LLP

(57) ABSTRACT

Embodiments of the disclosure may include a method for providing access within a patient that may include inserting a medical device through an opening of the patient. The medical device may include an overtube having a lumen and a slot and an elongate member disposed within the lumen of the overtube, wherein the elongate member may include an expandable member configured to expand and collapse. The method may further include positioning the medical device proximate a site in the patient, positioning the overtube relative to the elongate member such that a portion of the expandable member faces the slot, and the slot faces the site, and expanding the portion of the expandable member out of the slot and toward the site.

16 Claims, 17 Drawing Sheets

(56) References Cited

U.S. PATENT DOCUMENTS

| | | | |
|---|---|---|---|
| 6,364,892 B1 * | 4/2002 | Jervis | A61B 17/00234 |
| | | | 600/207 |
| 2004/0093005 A1 * | 5/2004 | Durcan | A61M 25/00 |
| | | | 606/194 |
| 2005/0222584 A1 * | 10/2005 | Kilpatrick | A61F 2/958 |
| | | | 606/108 |
| 2010/0063534 A1 * | 3/2010 | Kugler | A61B 17/221 |
| | | | 606/200 |
| 2011/0160539 A1 | 6/2011 | Robertson | |
| 2011/0264125 A1 * | 10/2011 | Wilson | A61B 90/02 |
| | | | 606/159 |
| 2013/0006282 A1 * | 1/2013 | Wilkinson | A61M 25/0082 |
| | | | 606/159 |
| 2014/0194920 A1 * | 7/2014 | Krahbichler | A61F 2/013 |
| | | | 606/200 |

\* cited by examiner

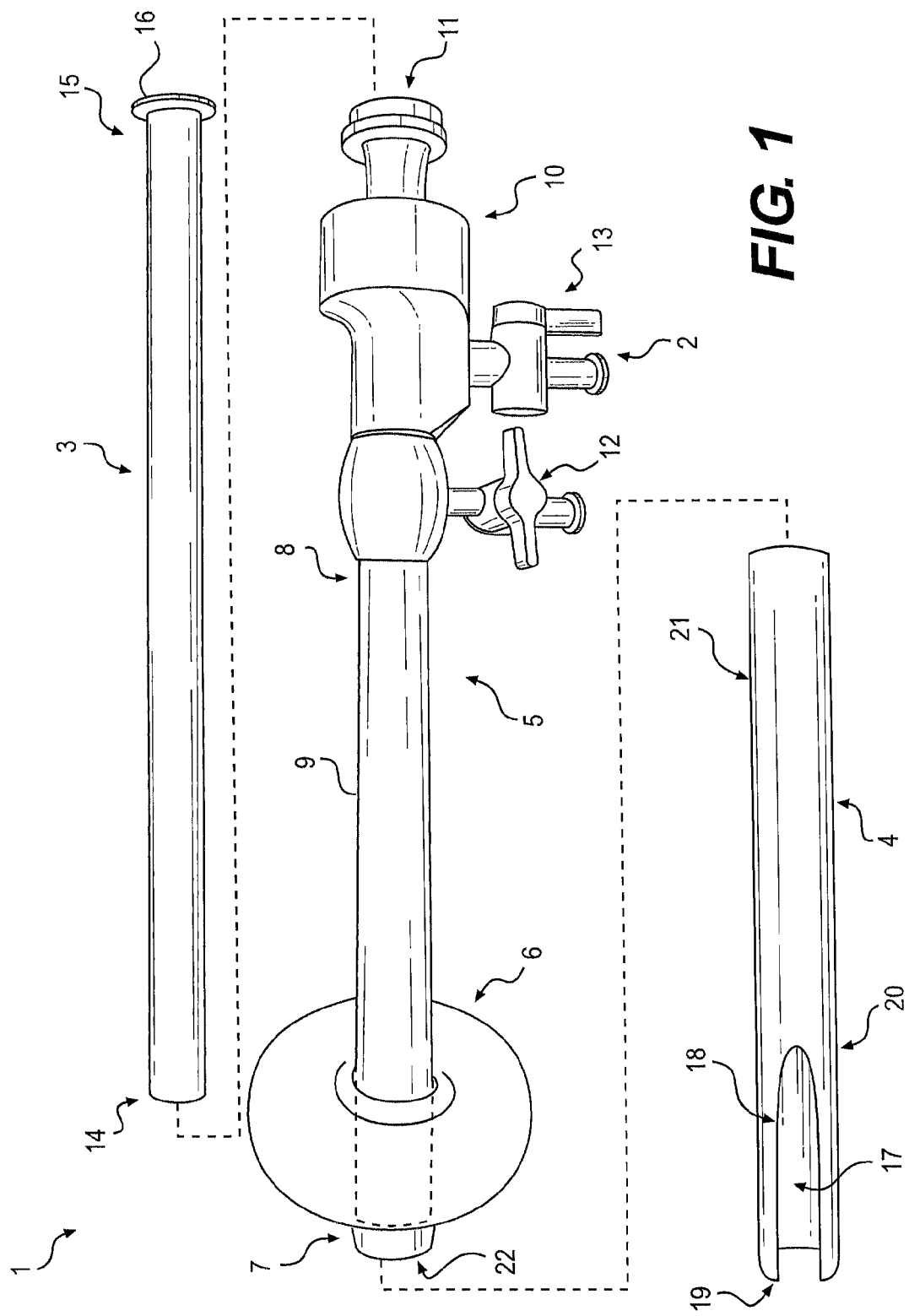

EXPANDABLE MEMBER DISSECTION PORT AND RELATED METHODS

PRIORITY

This application claims the benefit of priority of U.S. Provisional Application No. 61/726,992, filed on Nov. 15, 2012, the entire contents of which is incorporated by reference herein.

FIELD OF THE DISCLOSURE

Embodiments of the present disclosure include medical devices, and more particularly, medical devices having an expandable member and an overtube configured to manipulate the expandable member, and related methods of using such medical devices.

BACKGROUND OF THE DISCLOSURE

In general, it is desirable to minimize the invasiveness of medical procedures. These medical procedures may include therapeutic or diagnostic medical procedures. Invasive medical procedures are generally more expensive, and there is generally a greater risk of complication and discomfort for the patient. For example, open surgery, for a therapeutic or diagnostic purpose, is an invasive medical procedure with significant attendant risks. Since the performance of open surgery typically requires relatively large incisions, relatively large amounts of blood may be lost, the risk of infection may increase, and the potential for post-operative hernias may be higher. Furthermore, relatively large incisions require extended recovery times to allow the incisions to heal.

Certain medical procedures, such as laparoscopic procedures, are generally less invasive than open surgery. Laparoscopic cholesystectomy (lap choly) is a laparoscopic procedure that involves incisions through the skin to access various body organs. For example, lap choly may involve access through a small incision in the skin and placement of a port into the peritoneal cavity to allow removal of an inflamed gall bladder. A working instrument may be introduced into the body through the port. The working instrument may be a flexible instrument, such as an endoscope, introduced into the body to further access the inside of the body. A surgeon may use ports and working instruments to perform any desired therapeutic or diagnostic procedure at a work site inside the body.

Although growing capabilities of devices, such as endoscopes, allow physicians to perform an increasing variety of surgeries through minimally invasive routes, further refinements may allow even less traumatic surgical access and/or performance of traditional open surgical or laparoscopic procedures. Accordingly, methods and devices that improve access would be beneficial. The medical devices and related methods of the present disclosure are directed to improvements in the existing technology.

SUMMARY OF THE DISCLOSURE

In accordance with an embodiment, a method for providing access within a patient may include inserting a medical device through an opening of the patient. The medical device may include an overtube having a lumen and a slot and an elongate member disposed within the lumen of the overtube, wherein the elongate member may include an expandable member configured to expand and collapse. The method may further include positioning the medical device proximate a site in the patient, positioning the overtube relative to the elongate member such that a portion of the expandable member faces the slot, and the slot faces the site, and expanding the portion of the expandable member out of the slot and toward the site.

Various embodiments of the disclosure may include one or more of the following aspects: positioning the medical device proximate the site with the expandable member at least partially collapsed, positioning the overtube relative to the elongate member with the expandable member at least partially collapsed, manipulating a longitudinal position of the overtube relative to the elongate member before expanding the portion of expandable member out of the slot, wherein manipulating the longitudinal position of the overtube may include at least one of distally advancing the overtube relative to the elongate member and proximally retracting the overtube relative to the elongate member, wherein the longitudinal position of the overtube may be manipulated such that an entire axial length of the expandable member faces the slot, manipulating a radial position of the overtube relative to the elongate member before expanding the portion of expandable member out of the slot, wherein manipulating the radial position of the overtube may include rotating the overtube such that the slot faces the site, contacting the portion of the expandable member expanding out of the slot with the site, wherein expanding the portion of the expandable member may include delivering an inflation fluid through the elongate member and to the expandable member, probing the surgical site with a distal portion of the overtube by distally advancing the overtube relative to the elongate member, wherein the slot may be defined by a side-surface of the overtube, and wherein the slot may extend proximal to a distal face of the overtube.

In accordance with another embodiment, a method for providing access within a patient may include inserting a medical device through an opening in the patient. The medical device may include an overtube having a lumen and an elongate member disposed within the lumen of the overtube, wherein the elongate member may include an expandable member configured to expand and collapse. The method may also include positioning a distal face of the overtube between a proximal end and a distal end of the expandable member when the expandable member is at least partially collapsed, expanding the expandable member, and abutting the distal face of the overtube against the expandable member as the expandable member is expanded to advance a portion of the expandable member distal to a distal end of the elongate member.

Various embodiments of the disclosure may include one or more of the following aspects: maintaining a longitudinal position of the overtube as the expandable member is expanded, and wherein the lumen of the overtube may be completely surrounded by a wall of the overtube at the distal face.

In accordance with yet another embodiment, a medical device for providing access within a patient may include an overtube having a lumen and a slot defined by a side-surface of the overtube, and an elongate member configured to be disposed within the lumen of the overtube, the elongate member may include an expandable member at a distal end of the elongate member and configured to expand and collapse, wherein upon expansion of the expandable member, a first portion of the expandable member facing the slot may be configured to expand out of the slot, and a second portion of the expandable member facing away from the slot may be restricted from expansion by the overtube.

Various embodiments of the disclosure may include one or more of the following aspects: wherein the overtube may be configured to longitudinally and radially move relative to the elongate member to manipulate a position of the slot relative to the expandable member, wherein the overtube may include a distal face having a substantially arcuate cross-sectional shape, and wherein the slot may extend proximal to a distal face of the overtube.

BRIEF DESCRIPTION OF THE DRAWINGS

FIG. 1 illustrates a side view of a port component, an insert component, and an overtube of a dissection port, according to an exemplary disclosed embodiment;

DETAILED DESCRIPTION

Figure 1A:
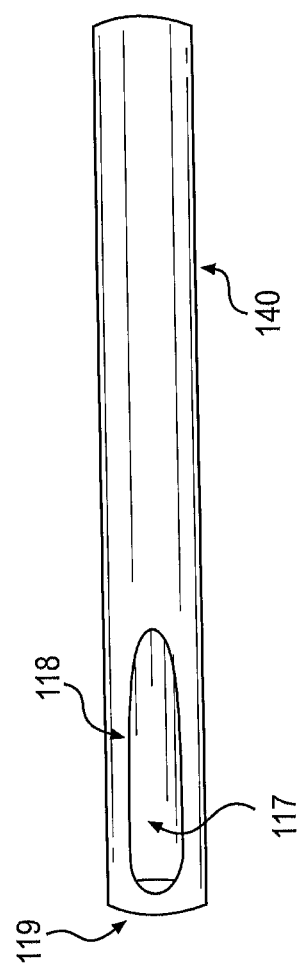
FIG. 1A illustrates a side view of another overtube, according to an exemplary disclosed embodiment.

Reference will now be made in detail to exemplary embodiments of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary dissection port 1. When used herein, "proximal" refers to a position relatively closer to the exterior of the body or closer to an operator, such as a surgeon, using dissection port 1. In contrast, "distal" refers to a position relatively further away from the operator using dissection port 1 or closer to the interior of the body.

FIG. 1 illustrates an exemplary dissection port 1 that may be used for any therapeutic or diagnostic endoscopic procedure. The phrase "endoscopic procedure" is broadly used to indicate any medical procedure that may be performed by inserting an endoscope, guide tube, catheter, or any other medical device into the body through any anatomic opening. Embodiments of the current disclosure may be applicable to any application where a medical device is inserted into the body through an anatomic opening (e.g., an incision or a natural orifice). For example, embodiments of the current disclosure may be used in natural orifice transluminal endoscopic surgical (NOTES) procedures or single incision laparoscopic surgical (SILS) procedures.

In a NOTES procedure, a working instrument may be introduced into the body through a body orifice (e.g., mouth, anus, nose, urethra, vagina, etc.). Therefore, a NOTES procedure may allow access to various body organs through an incision in a luminal wall without having to puncture the skin. After one or more working instruments pass through the natural orifice and are positioned at a desired work site within the body, the operator may perform any desired therapeutic or diagnostic procedure at the work site.

In a SILS procedure, the operator may create a single incision through the skin of the patient to access the desired work site. The incision acts as a single entry point. After one or more working instruments pass through the single entry point and are positioned at the desired work site in the body, the operator may perform any desired therapeutic or diagnostic procedure at the work site.

Dissection port 1 may be used for other procedures, such as, but not limited to, procedures for single access site (SAS) laparoscopic surgery, single port access (SPA) surgery, single port laparoscopy (SPL), single site access (SSA) surgery, one-port umbilical surgery (OPUS), visibly scarless urologic surgery (VSUS), single laparoscopic port procedure (SLiPP), natural orifice trans umbilical surgery (NOTUS), trans umbilical endoscopic surgery (TUES), trans umbilical laparoscopic assisted (TULA) surgery, embryonic natural orifice transluminal endoscopic surgery (E-NOTES), single-incision multiport laparoendoscopic surgery (SIMPLE), laparo-endoscopic single site surgery (LESS), and single port incisionless conventional equipment-utilizing surgery (SPICES), or used as one of several ports in laparoscopic surgery.

According to an exemplary embodiment, dissection port 1 may include a port component 2, an insert component 3 that may be inserted into port component 2, and an overtube 4. As described below, dissection port 1 may be inserted into a patient to separate or dissect tissue layers in the patient. By separating the tissue layers, dissection port 1 may create a working space between the tissue layers, and dissection port 1 may direct insufflation fluid into the working space to maintain the separation of the tissue layers. Dissection port 1 may be made of any suitable material capable of being inserted into the body, e.g., a suitable biocompatible material. Dissection port 1 may be curved, bent, deformable, and/or steerable, etc. to angle the dissection port 1 as desired for a procedure.

Port component 2 may include an elongate member 5 and an expandable member 6. Elongate member 5 may include a distal end 7 and a proximal end 8, and may be rigid, malleable, or flexible. Any of the components of dissection port 1 may be reinforced by, for example, braiding, coiling, discrete fibers, material blends, etc. Any of the cannulas or tubes of dissection port 1 may comprise variable stiffness at portions along the length. Elongate member 5 may also include a cannula 9, a housing 10, and a hollow cavity or bore (not shown) extending through cannula 9 and housing 10. Housing 10 may be disposed proximal to cannula 9 and may include one or more valves or other devices that may be controlled by the operator or other user.

Cannula 9 may be a tubular member configured to be at least partially inserted into an opening of the patient, such as a natural orifice in the body (e.g., mouth, rectum, anus, nose, urethra, umbilicus, vagina, etc.) or an incision created by the operator. Elongate member 5 may be advanced through the opening in the patient such that distal end 7 may be positioned at or near the working space.

The bore of elongate member 5 may extend longitudinally (i.e., axially) between distal end 7 and proximal end 8 of elongate member 5. The bore may extend from an opening at a distal end of cannula 9 to a port opening 11 in housing 10 at proximal end 8 of elongate member 5. Insert component 3 may be inserted into the bore.

Elongate member 5 may include one or more lumens extending longitudinally therethrough, and such lumens may or may not extend through distal end 7 and/or proximal end 8 of the elongate member 5. The one or more lumens may provide for the delivery of various instruments or fluids out the distal end 7 to help in the dissection of tissue. For example, elongate member 5 may include an inflation lumen (not shown) extending longitudinally through elongate member 5, but not extending through distal end 7 or the housing 10 at the proximal end 8 of elongate member 5. The inflation lumen may be a cavity in elongate member 5 through which a fluid, such as a liquid or gas, may pass to expand (inflate) and contract or collapse (deflate) expandable member 6. For example, the inflation fluid may be air, water, carbon dioxide, or saline solution. The inflation lumen may be fluidly connected at one end to a first valve 12 disposed on housing 10 and at an opposite end to expandable member 6. The inflation lumen may extend through housing 10 and cannula 9 of elongate member 5. First valve 12 may permit fluid to enter the inflation lumen and may prevent fluid from exiting from inside the inflation lumen. First valve 12 may also allow the operator to vent fluid from inside the inflation lumen and expandable member 6.

For example, a source of the inflation fluid (not shown), such as a pump or syringe, may be connected to first valve 12 to direct inflation fluid into the inflation lumen and expandable member 6. After expandable member 6 is expanded to a desired expanded configuration, the source of the inflation fluid may be disconnected from first valve 12, and then first valve 12 may prevent the inflation fluid from exiting the inflation lumen and the expandable member 6. After removing the source of the inflation fluid, the operator may also control first valve 12 to release or vent inflation fluid from the inflation lumen and expandable member 6, and may collapse expandable member 6 to a collapsed position.

The phrase "expandable member" is used in a broad sense to denote any expandable structure, such as a balloon or other inflatable structure, regardless of the elasticity of the material comprising the structure. For example, the phrase "expandable member" may denote a thin-walled structure made of material of low elasticity (which does not stretch significantly during inflation) or highly elastic material (which does stretch significantly during inflation). For example, expandable member 6 may be made from polyethylene terephthalate (PET), polyurethanes, polyethylenes and ionomers, copolyesters, rubbers, polyamides, silicone, latex, or any other suitable materials known in the art. Expandable member 6 may be mechanically, electrically, pneumatically or hydraulically expanded and collapsed without departing from the scope of the disclosure.

Figure 2:
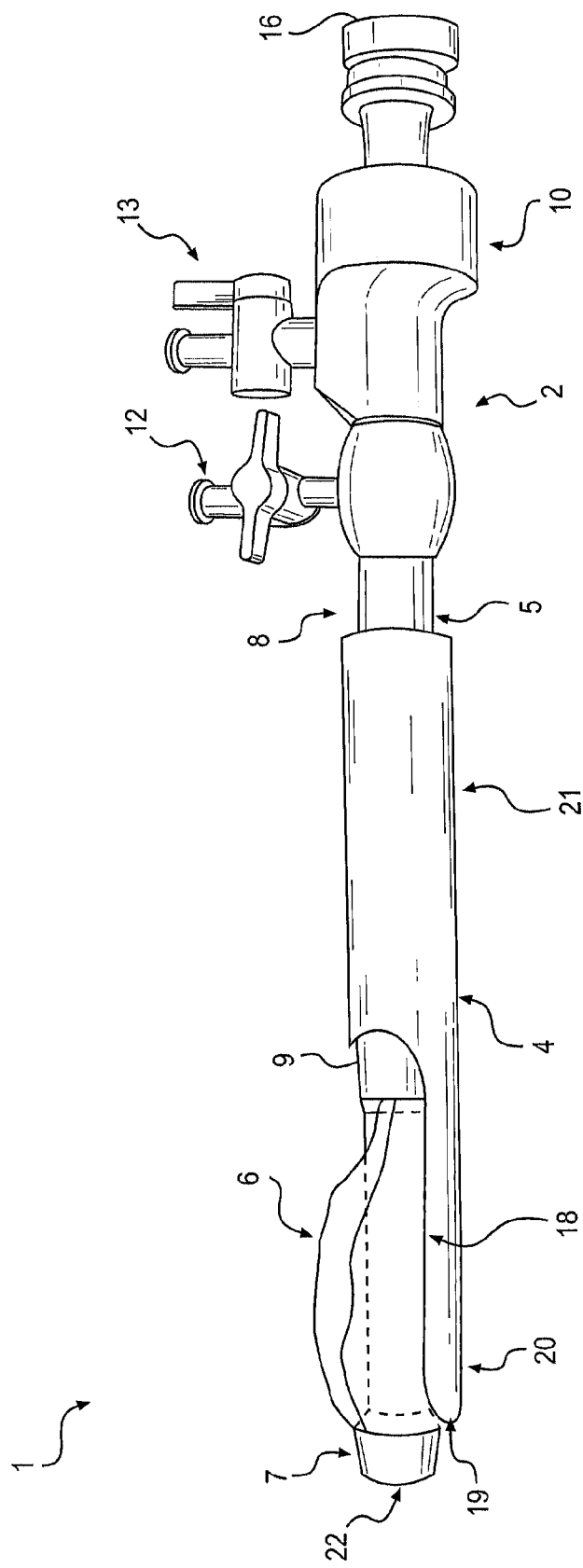
FIG. 2 illustrates a side view of the dissection port of FIG. 1 with the port component disposed in the overtube, according to an exemplary disclosed embodiment.

Expandable member 6 may be in a desired expanded configuration (e.g., FIG. 1), and in the collapsed configuration (FIG. 2). The particular expanded exterior configuration of expandable member 6, such as the volume, width, depth, radius, length, or other dimension, may be selected depending on the particular circumstances of use. For example, expandable member 6 in its expanded configuration may be toroidal or doughnut-shaped (e.g., FIG. 1). In certain other embodiments, however, expandable member 6 may be spherical or cylindrical, in other words, extending farther along the length of cannula 9. Moreover, the outer profile of expandable member 6 may be any suitable shape, such as, for example, circular, oval-shaped, elliptical, teardrop-shaped, triangular, square-shaped, conical and the like. Expandable member may be asymmetric in cross-sectional profile. Expandable member 6 may also include a hole through its center, through which cannula 9 may pass and may be attached. Inflatable, expandable member 6 may be reinforced to prevent leakage or wear. Such reinforcement may include wall thickness, coatings, reinforced layer, braiding, coils, ribs etc. Expandable member 6 may alternatively be expanded mechanically and include a cage or basket, so long as it increases the profile of cannula 9 locally. If a cage or basket, then additional actuation elements, such as one or more pull wires may be incorporated to expand the device.

Housing 10 may also include a second valve 13 fluidly connected to the bore extending through elongate member 5. Second valve 13 may be configured to permit fluid to enter and may prevent fluid from exiting the bore or lumens in insert component 3. Second valve 13 may also allow the operator to vent fluid from inside the bore of elongate member 5 or the lumens in insert component 3.

For example, insufflation fluid may be directed through second valve 13, and through the bore of elongate member 5 or the lumens in insert component 3 placed within the bore. The insufflation fluid may be supplied to the working space, for example, to maintain or further extend the separation between tissue layers after dissecting the tissue layers. The insufflation fluid may be a liquid or gas, such as air, water, carbon dioxide, or saline solution. A source of the insufflation fluid, such as a pump or syringe, may be connected to second valve 13 to direct the insufflation fluid into the bore of elongate member 5 or the lumens in insert component 3, which directs the insufflation fluid through a respective opening of the bore or the lumens in insert component 3 at distal end 7 of elongate member 5. After providing a desired amount of insufflation fluid, the source of the insufflation fluid may be disconnected from second valve 13. After removing the source of the insufflation fluid, second valve 13 may prevent the insufflation fluid from exiting the bore, the lumens in insert component 3, and/or the working space. Also, after removing the source of the insufflation fluid, the operator may control second valve 13 to release or vent insufflation fluid from the bore, the lumens in insert component 3, and/or the working space.

Insert component 3 may be configured to be slidably inserted into the bore of elongate member 5, and may be rigid, malleable, or flexible. Insert component 3 may include a distal end 14 and a proximal end 15. Insert component 3 may also include a flange 16 at proximal end 15 of insert component 3. When insert component 3 is disposed inside the bore of elongate member 5, flange 16 may abut proximal end 8 of elongate member 5 or a proximal end of housing 10 to hold insert component 3 in place longitudinally.

As alluded to above, one or more lumens may extend longitudinally through insert component 3. The lumens may extend through distal end 14 and proximal end 15 of insert component 3. The lumens may include one or more of an aspiration lumen, an irrigation lumen, an illumination lumen, a viewing lumen, a working lumen, and the like. One or more working instruments may be delivered through the lumens of insert component 3. The working instruments may include, for example, end effectors, an optical device, devices to assist in orienting or directing other working instruments, devices to dissect tissue, or any other suitable medical instrument.

Overtube 4 of dissection port 1 may be configured to slidably engage with port component 2 and manipulate expandable member 6. Overtube 4 may include a lumen 17 into which elongate member 5 and expandable member 6 may be inserted. It should be appreciated that lumen 17 may include a suitable diameter such that overtube 4 may move longitudinally and radially relative to elongate member 5. That is, overtube 4 may be configured to move in a distal direction and a proximal direction relative to cannula 9 and expandable member 6, and may be configured to rotate relative to cannula 9 and expandable member 6. Overtube 4 may also include one or more displacement slots 18 positioned on a side-surface of overtube 4. As will be discussed in more detail below, slot 18 may be configured to manipulate various aspects of expandable member 6, such as, for example, its shape, size, position, and/or location.

In certain embodiments, overtube 4 may include a distal face 19 completely open into lumen 17. Distal end 7 of elongate member 5 may be configured to exit distal face 19 of overtube 4 when overtube 4 is proximally retracted relative to elongate member 5. In addition, slot 18 may extend to distal face 19. As such, a distal portion 20 of overtube 4 may be bound by a proximal end of slot 18 and distal face 19, and may include a substantially arcuate cross-sectional shape. In certain other embodiments, however, distal portion 20 may include any other suitable cross-sectional shape depending on, for example, the shape of overtube 4 and/or slot 18. Moreover, although one slot 18 is illustrated, it should be appreciated that more than one slot 18 may be positioned on any location of overtube 4 to control a plurality of portions of expandable member 6. In certain embodiments, dissection port 1 may include more than one overtube 4.

FIG. 1A illustrates an overtube 140 for use with dissection port 1, according to an exemplary disclosed embodiment. Overtube 140 may include similar features and applications as overtube 4, but may include a slot 118 extending proximal to a distal face 119 of overtube 140. A proximal end and a distal end of slot 118 may be bound by the walls of overtube 140. In certain embodiments, distal face 119 may be completely open into a lumen 117 of overtube 140, and thus, distal end 7 of elongate member 5 may be configured to exit distal face 119 of overtube 140 when overtube 140 is proximally retracted relative to elongate member 5. In other embodiments, distal face 119 may be at least partially closed by a wall of overtube 140 to restrict access into lumen 117. Accordingly, elongate member 5 may be restricted from exiting distal face 119, and at least a portion of expandable member 6 may be restricted from exiting distal face 119 when inflated. Moreover, although one slot 118 is illustrated, in certain embodiments, more than one slot 118 may be positioned on any location of overtube 140. For example, two slots 118 may be positioned on substantially opposite sides of overtube 140.

It should also be appreciated that dissection port 1 may include one or more features of the dissection port disclosed in U.S. patent application Ser. No. 12/979,628 to Robertson, which is incorporated herein by reference in its entirety.

FIG. 2 illustrates dissection port 1 including port component 2 disposed within lumen 17 of overtube 4. FIG. 2 also illustrates an exemplary embodiment of expandable member 6 in the collapsed configuration. Overtube 4 may be configured to house at least a portion of expandable member 6 when expandable member 6 is in the collapsed configuration. A portion of expandable member 6 may be exposed to an external environment of dissection port 1 and may be free to exit lumen 17 via slot 18, while another portion of expandable member 6 may be shielded from the external environment by overtube 4 and may be restricted from exiting lumen 17. It should also be appreciated that overtube 4 may be distally advanced relative to elongate member 5 such that a proximal portion 21 of overtube 4 may house an entirety of expandable member 6 in the collapsed position. Proximal portion 21 may be bound, for example, by the proximal end of slot 18 and a proximal end of overtube 4.

Figure 3A:
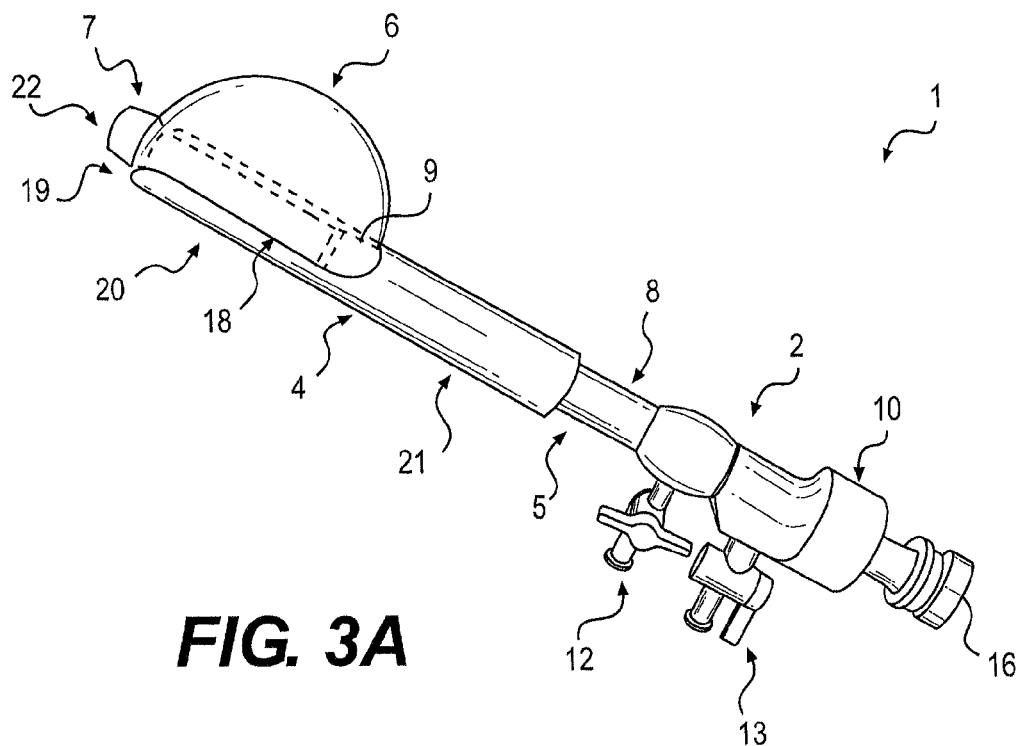
FIG. 3A illustrates another side view of the dissection port of FIG. 1 with the port component disposed in the overtube, and an expandable member of the port component in an expanded configuration, according to an exemplary disclosed embodiment.

FIG. 3A illustrates dissection port 1 including another configuration of port component 2 disposed within lumen 17 of overtube 4. FIG. 3A also illustrates an exemplary embodiment of an expansion of expandable member 6 manipulated by overtube 4. When expandable member 6 is in the collapsed configuration, or is partially inflated with sufficient clearance from overtube 4 to allow relative movement between overtube 4 and elongate member 5, the operator may position overtube 4 such that a desired portion of expandable member 6 is capable of exiting slot 18 and/or distal face 19. For example, the operator may distally advance, proximally retract, and/or rotate overtube 4 to position slot 18 and/or distal face 19 relative to expandable member 6. Expandable member 6 may then be inflated, thereby effectuating expansion of the portions of expandable member 6 facing slot 18 and/or distal face 19 outwardly from lumen 17 of overtube 4, while the portions of expandable member 6 not facing or facing away from slot 18 and/or distal face 19 may be restricted from expansion by the walls defining lumen 17. Accordingly, overtube 4 may be positioned such that only certain portions of expandable member 6 may expand from elongate member 5. For example, the exemplary embodiment of FIG. 3A illustrates that only portions of expandable member 6 on a side substantially opposite that of first valve 12 and second valve 13 may expand from lumen 17 of overtube 4. It should be appreciated, however, that overtube 4 may be moved to any other suitable position to manipulate the orientation and direction of the portions of expandable member 6 expanding from lumen 17. For instance, overtube 4 may be advanced to a position more distal than that illustrated in FIG. 3A, such that a volume of expandable member 6 expanded through slot 18 may be decreased. That is, an axial length of expandable member 6 that may be expanded from slot 18 may be shortened by distally advancing overtube 4. Proximal portion 21 of overtube 4 may cover and thus restrict from expansion certain portions of expandable member 6 proximal to slot 18. In some embodiments, overtube 4 may include any suitable markers and/or indicators to provide a circumferential position of slot 18 relative to elongate member 5. The markers and/or indicators may show a direction to which slot 18 faces. Furthermore, one or both of elongate member 5 and overtube 4 may include markers and/or indicators to provide a longitudinal position of overtube 4 relative to elongate member 5. The markers and/or indicators may show an axial location of slot 18 along elongate member 5 and relative to expandable member 6.

Figure 3B:
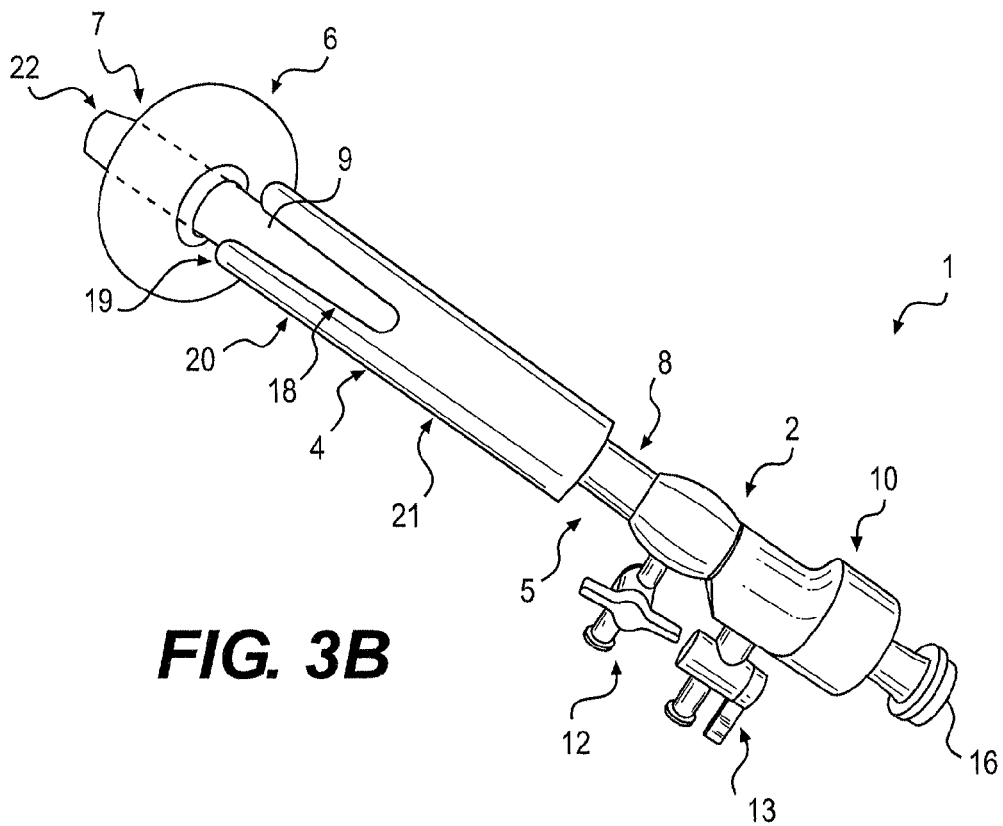
FIG. 3B illustrates another side view of the dissection port of FIG. 1 with the port component disposed in the overtube, and the expandable member of the port component in another expanded configuration, according to an exemplary disclosed embodiment.

FIG. 3B illustrates dissection port 1 including yet another configuration of port component 2 disposed within lumen 17 of overtube 4. As shown in FIG. 3B, overtube 4 may be proximally retracted relative to port component 2 such that no portion of expandable member 6 is restricted from expansion by overtube 4. The operator may pull back on overtube 4, or alternatively, push port component 2 forward, until distal face 19 of overtube 4 is proximal expandable member 6. Inflation fluid may then be delivered to expandable member 6 to further expand expandable member 6 around an entire circumference of cannula 9. As shown in FIG. 3B, an entire outer surface of expandable member 6 may be external to overtube 4, and therefore, expandable member 6 may be free to expand to its fully-expanded configuration. For example, FIG. 3B illustrates that expandable member 6 may fully expand to its donut or toroidal shape. It should be appreciated, however, that expandable member 6 may be partially inflated to any configuration between its collapsed configuration and its fully-expanded configuration when no portion of expandable member 6 is restricted by overtube 4 or when certain portions of expandable member 6 are restricted by overtube 4.

The operator may control the position of overtube 4 after overtube 4 has manipulated the expanded configuration of expandable member 6. The operator may first position slot 18 of overtube 4 over expandable member 6 and deliver inflation fluid to control expansion of certain portions of expandable member 6 (FIG. 3A). The operator then may proximally retract overtube 4, or distally advance port component 2, such that expandable member 6 may be completely free from restriction by overtube 4. If desired, the operator may subsequently deliver inflation fluid to expandable member 6 to inflate expandable member 6 to its fully-expanded configuration (FIG. 3B).

In other embodiments, dissection port 1 may be delivered to a target location with overtube 4 positioned over expandable member 6 while expandable member 6 is in its collapsed configuration (e.g., FIG. 2). The operator may then proximally retract overtube 4, or distally advance port component 2, and deliver inflation fluid to expandable member 6 to inflate expandable member 6 to its fully-expanded configuration (FIG. 3B).

FIGS. 4-8 depict a method for providing surgical access to a site within a patient using dissection port 1, according to an exemplary embodiment. For the purpose of illustration only, the method is described in the context of placing an access port through the abdominal wall by separating the tissue layers with balloon dissection to perform a surgical procedure inside the abdominal wall. Variations on the described embodiment (and in the apparatus employed to perform it) are useful for performing other medical procedures throughout the body.

Figure 4:
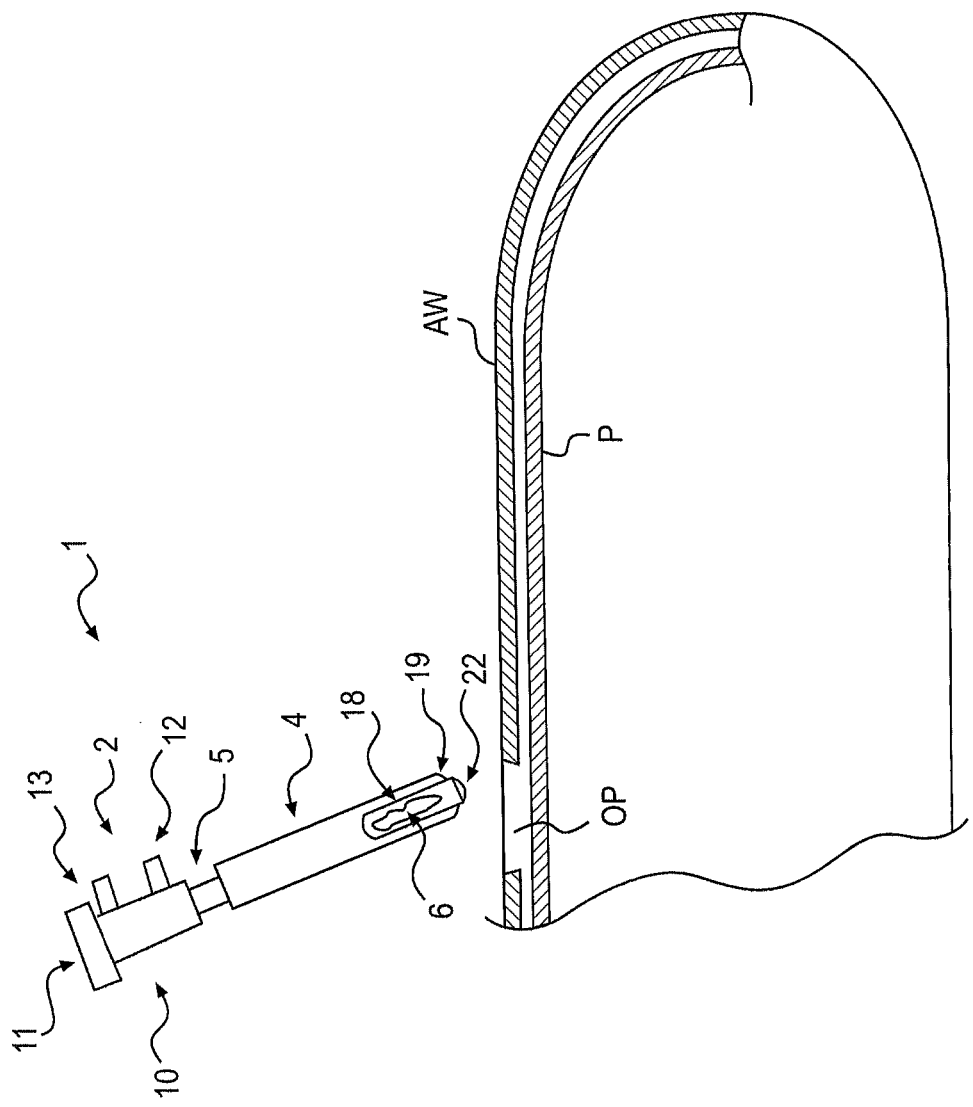
FIG. 4 illustrates a dissection port and a cross-sectional view of an opening in an abdominal wall of a patient, according to an exemplary disclosed embodiment.

As shown in FIG. 4, an incision, e.g., about 5-20 mm long, is made in the epithelium of an abdominal wall AW. Additional blunt or sharp dissection forms an opening OP. Alternatively, such as in a NOTES procedure, the opening OP is made after passing the dissection port 1 through a natural orifice, e.g., mouth, anus, nose, urethra, vagina, etc., and making an incision in a lumenal wall. At this point, expandable member 6 is in a substantially collapsed configuration.

Figure 5:
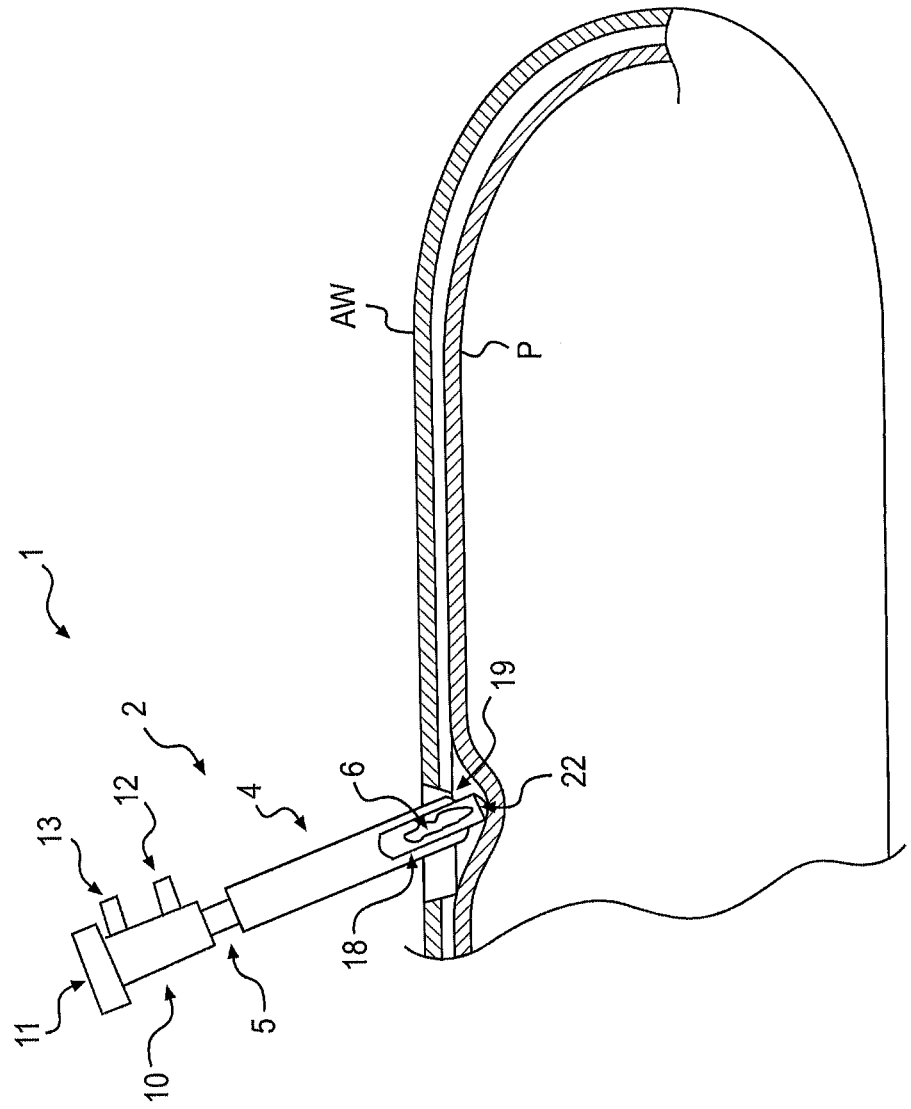
FIG. 5 illustrates a distal end of the dissection port of FIG. 4 inserted into the opening in the patient, according to an exemplary disclosed embodiment.

As shown in FIG. 5, dissection port 1 with port component 2 disposed within overtube 4 may be inserted into the opening OP to bring a distal face 22 of elongate member 5, or alternatively, distal face 19 of overtube 4, into contact with the peritoneum P. The bore of elongate member 5 may be empty (i.e., without insert component 3 inserted into the bore), or insert component 3 may be placed in the bore. Also at this point, expandable member 6 may be in a substantially collapsed configuration.

At any time during the steps shown in FIGS. 4-8, insert component 3 may include a blunt and/or rounded tip (an obturator) and may be inserted into the bore of elongate member 5, and the blunt and/or rounded tip of insert component 3 may be brought into contact with the peritoneum P or other body tissues. The obturator may include zero lumens. Alternatively, insert component 3 with one or more lumens may be replaced and/or inserted into the bore of elongate member 5, and a working instrument with a blunt and/or rounded tip (similar to the obturator described above) may be inserted into one of the lumens in insert component 3. The blunt and/or rounded tip of insert component 3 or the working instrument may be brought into contact with the peritoneum P or other body tissues. Other tips are contemplated for insert component 3 such as a flat wide tip.

Additional pressure may be exerted on the proximal end of overtube 4, proximal end 8 of elongate member 5, proximal end 15 of insert component 3 with the blunt and/or rounded tip, and/or the proximal end of the working instrument with the blunt and/or rounded tip, which presses against the peritoneum P, thereby separating the part of the peritoneum in the immediate vicinity of the opening OP from other body tissues.

Figure 6:
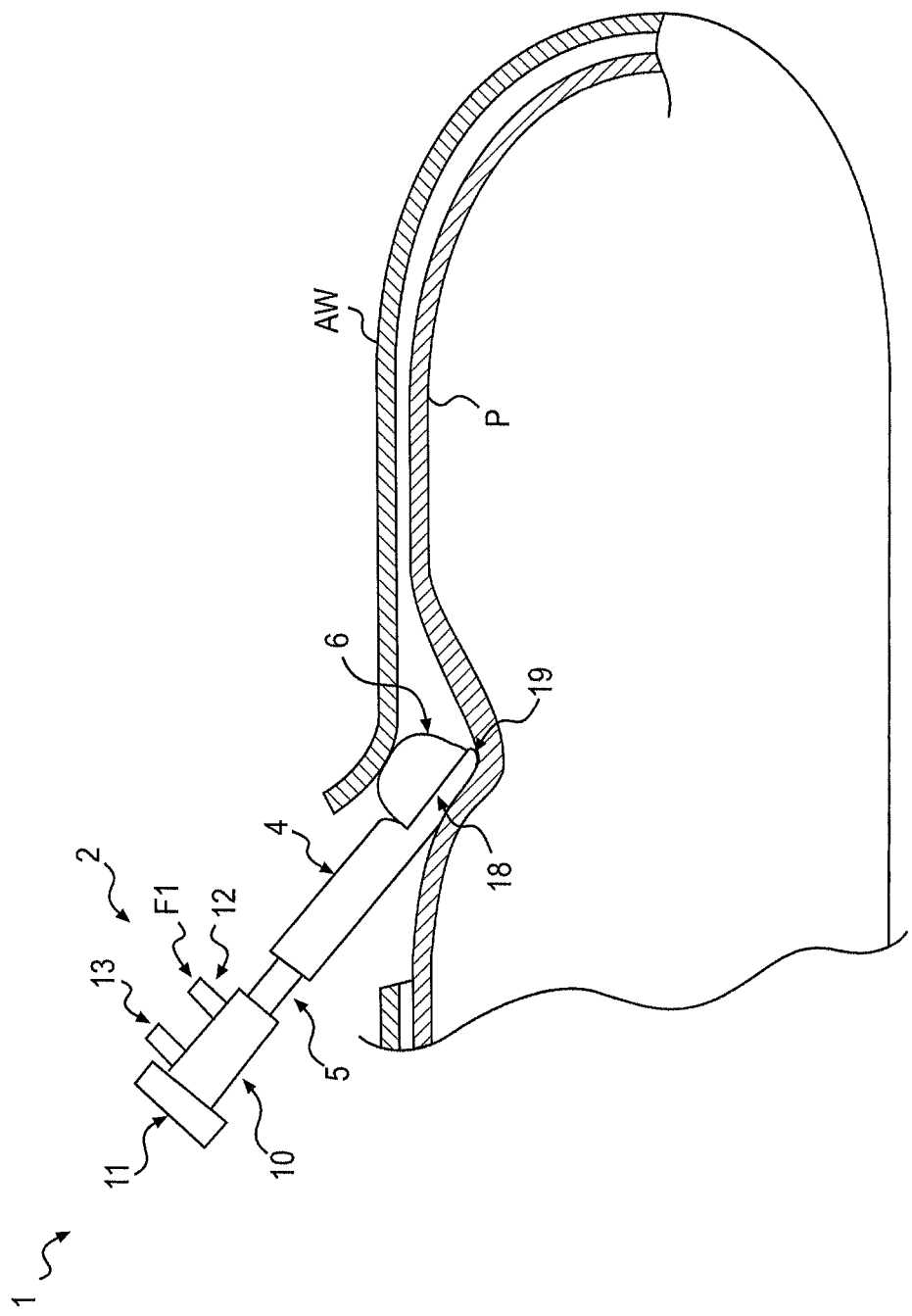
FIG. 6 illustrates an expandable member of the dissection port of FIG. 4 expanded to separate tissue layers in the patient, according to an exemplary disclosed embodiment.

As shown in FIG. 6, overtube 4 may be manipulated such that expandable member 6 may be expanded in a desired direction. Overtube 4 may be appropriately positioned with slot 18 facing a radial direction in which expandable member 6 may expand. Moreover, overtube 4 may be moved to an appropriate longitudinal position relative to elongate member 5 to control a volume of expandable member 6 that may be expanded through slot 18. As shown in FIG. 6, for example, an entire axial length of expandable member 6 may face slot 18 and thus expand out of slot 18. It should be appreciated, however, that overtube 4 may be distally advanced to decrease the axial length of expandable member 6 that may expand out of slot 18.

Figure 7:
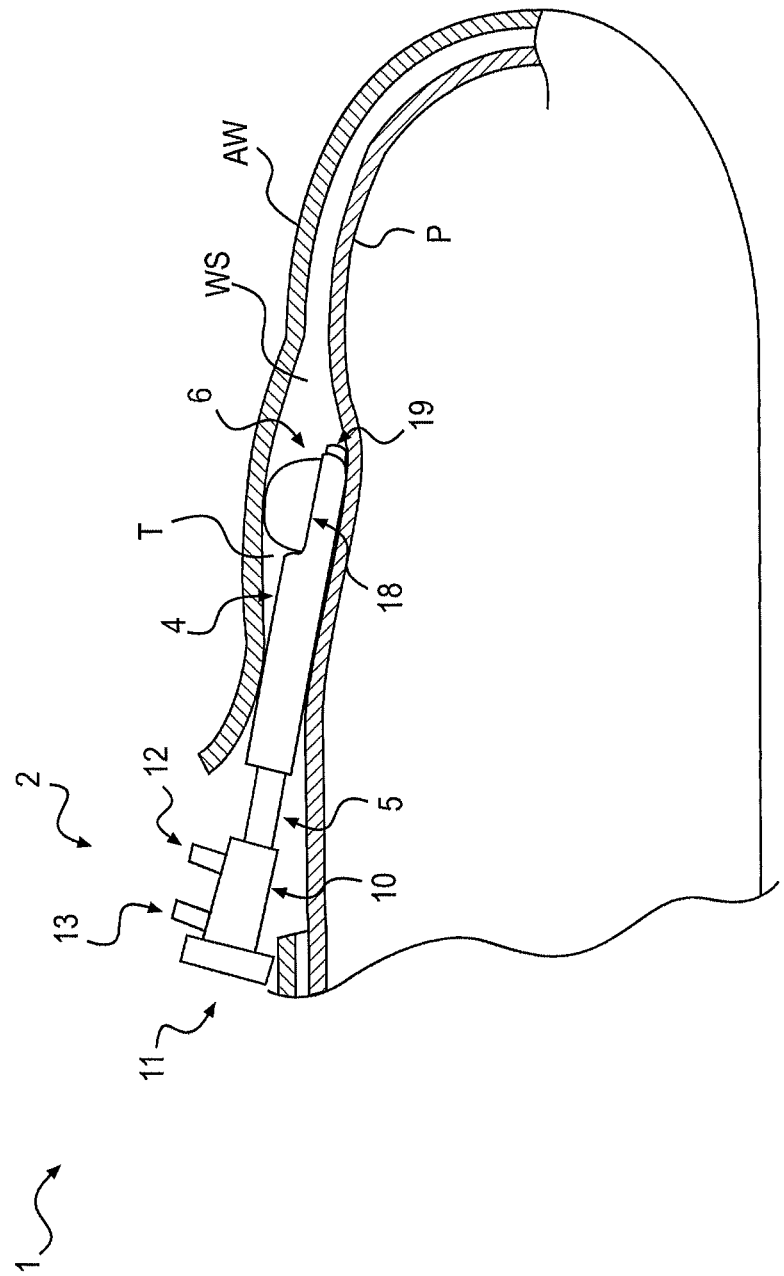
FIG. 7 illustrates the expandable member of the dissection port of FIG. 4 expanded to create a working space in the patient, according to an exemplary disclosed embodiment.
Figure 8:
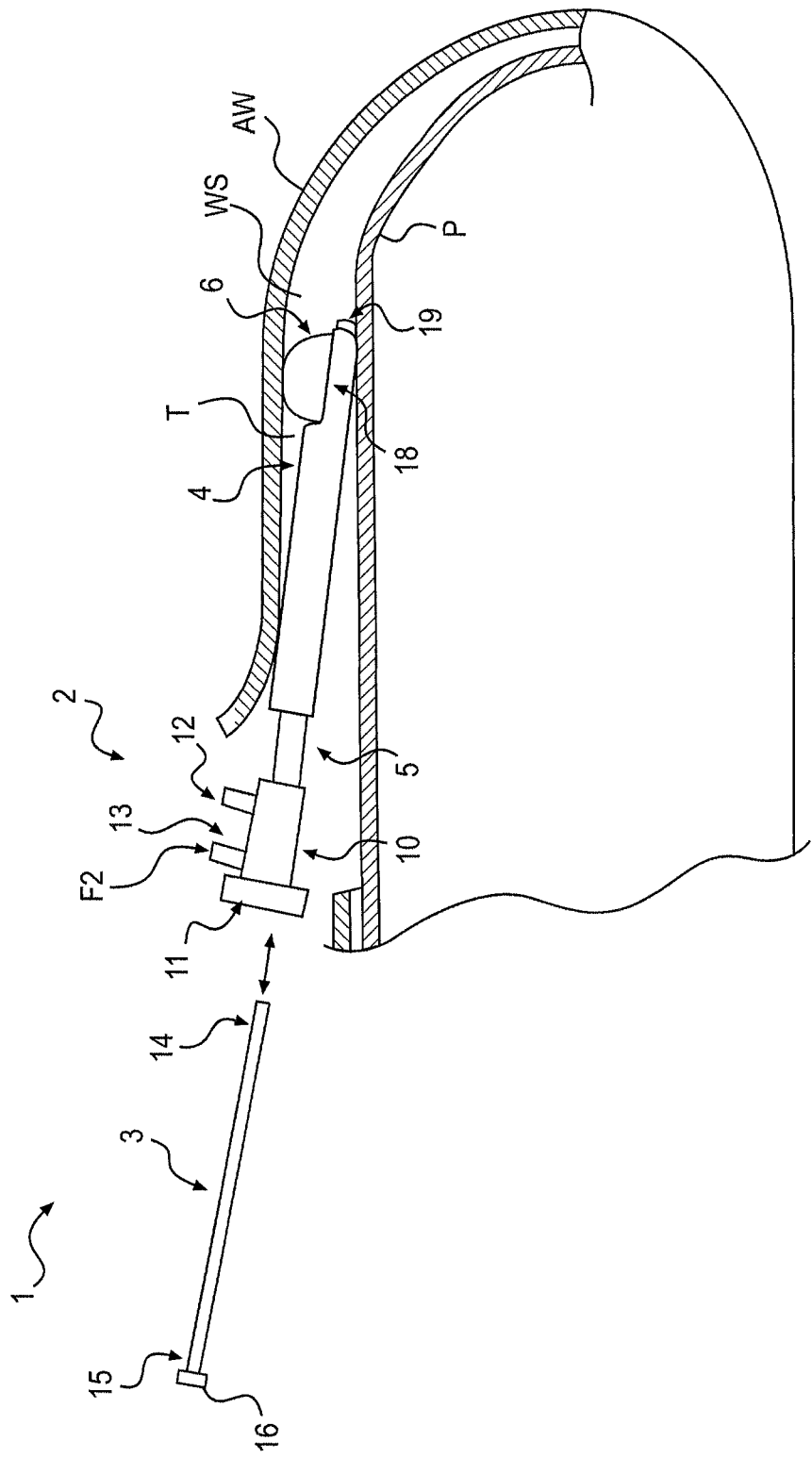
FIG. 8 illustrates the dissection port of FIG. 4 with an interchangeable insert component, according to an exemplary disclosed embodiment.

Inflation fluid may then be directed to first valve 12 (indicated by arrow F1), and expandable member 6 may be at least partially expanded with the inflation fluid. Expandable member 6 may expand toward a target tissue layer, for example, the abdominal wall AW, and may progressively push against the abdominal wall AW to create an increasing volume of retroperitoneal space between the abdominal wall AW and the adjacent tissues along the dissection tract. Accordingly, by manipulating overtube 4, the operator may selectively target one or more tissue layers to be moved by expandable member 6. Moreover, manipulating overtube 4 may also selectively protect certain tissue layers from disruption by expandable member 6. For example, and as illustrated in FIGS. 7 and 8, overtube 4 may be positioned such that the abdominal wall AW may be pushed by expandable member 6 to increase the volume of retroperitoneal space, while the peritoneum P opposite expandable member 6 may be shielded from contact and disruption by expandable member 6. It should also be appreciated that slot 18 may face the peritoneum P, and expandable member 6 may be inflated to expand toward the peritoneum P and push against the peritoneum P to create an increasing volume of retroperitoneal space. In such an application, the abdominal wall AW may be shielded from contact and disruption by expandable member 6.

Expandable member 6 may be at least partially expanded and at least partially collapsed a number of times to progressively separate the tissue layers. Also, the operator may use an optical device, for example, an optical device delivered through the bore of elongate member 5 or a lumen of insert component 3, to observe the dissection of the tissue layers, and may decide whether and how much to expand and/or collapse expandable member 6 based on the observations. The operator may also observe the manipulation and treatment of the tissue to determine where to reposition expandable member 6. The operator may also use tactile feedback from expanding, collapsing, and/or moving expandable member 6 to determine whether and how much to expand and/or collapse expandable member 6.

For example, after expanding expandable member 6 the first time (thereby partially dissecting the tissue layers), the inflation fluid in expandable member 6 may be vented and expandable member 6 may return to an at least partially collapsed configuration. The portion of the abdominal wall AW (or the peritoneum P) that was separated by expandable member 6 may remain detached from the adjacent tissue layer. Dissection port 1, including expandable member 6 in the collapsed configuration, may then be manipulated to advance distal end 7 of elongate member 5, or alternatively, distal face 19 of overtube 4, to the limit of the created retroperitoneal space. Expandable member 6 may then be expanded again, thereby increasing the extent of the detached part of the abdominal wall AW (or the peritoneum P). This "tunneling" process of collapsing expandable member 6, advancing distal end 7 of elongate member 5, or distal face 19 of overtube 4, to the limit of the detached part of the abdominal wall AW (or the peritoneum P), holding distal end 7 of elongate member 5, or distal face 19 of overtube 4, in position, and expanding expandable member 6 again, may be repeated until the created retroperitoneal space includes a desired work site. Expandable member 6 may also be at least partially expanded and collapsed to provide support to retract tissue away from a work site.

At any time before or during the procedure illustrated in FIGS. 4-7, the operator may insert and/or replace insert component 3 inside the bore of port component 2, as shown in FIG. 8. The operator may also insert and/or replace the working instruments in the lumens of insert component 3 in port component 2. One such working instrument may include, for example, a device to assist in advancing or redirecting dissection port 1 or port component 2, such as by pulling or retracting tissue, or initiating a new plane of dissection. The new plane of dissection may be located between tissue layers that are different from the tissue layers previously separated by the expansion of expandable member 6. For example, the new plane of dissection may be initiated by at least partially collapsing expandable member 6, pulling or pushing port component 2 in a new direction, and expanding expandable member 6. Alternatively, the new plane of dissection may be initiated by using a deflectable portion of a working instrument, e.g., with at least one of a blunt tip, an end effector, such as a grasper, or an expandable member on a working instrument. Insert component 3 and the working instruments to be inserted may be selected based on the intended use for the working instruments and the tasks to be completed.

As shown in FIG. 7, when expandable member 6 is inflated, expandable member 6 may form a seal to limit the escape of fluids, such as insufflation fluid and body fluids, from the working space WS within the patient by providing a substantially fluid-tight seal of the tunnel T with the tissue contacting an outer surface of expandable member 6 and overtube 4. The seal may be used to block flow of any type of fluid, such as the insufflation fluid, water, saline, body fluids (e.g., gastric fluids, colonic fluids, blood, etc.), etc.

As shown in FIG. 8, the working space WS at the desired work site may then be insufflated by directing insufflation fluid (indicated by arrow F2) through second valve 13 into the working space WS. As described above, the insufflation fluid may be directed from second valve 13 either through the bore in elongate member 5 of port component 2 or through a lumen in insert component 3.

According to another embodiment, dissection port 1 may be used for a transvaginal single-port sacrocolpopexy procedure. In such a procedure, the incision may be made in the vaginal wall using dissection port 1, as in FIG. 4. Then, expandable member 6 may be used to dissect tissue to create a tunnel outside and parallel to the vagina using dissection port 1 with or without any appropriate insert component 3 and/or working instruments, as in FIGS. 5-8. In addition, overtube 4 may be appropriately positioned to direct expandable member 6 to a target tissue plane to be dissected. After the retroperitoneal cavity is fully developed to allow access to the sacral promontory, a mesh or tissue graft may be delivered using one of the working instruments inserted into a lumen in insert component 3 or through the bore in elongate member 5 (with or without insert component 3 in the bore). One or more other working instruments may be inserted through the lumen, or through the bore to attach the mesh to tissue in the body over the sacrum, such as the anterior longitudinal ligament, or to the vagina, and/or to observe the procedure.

Figure 9A:
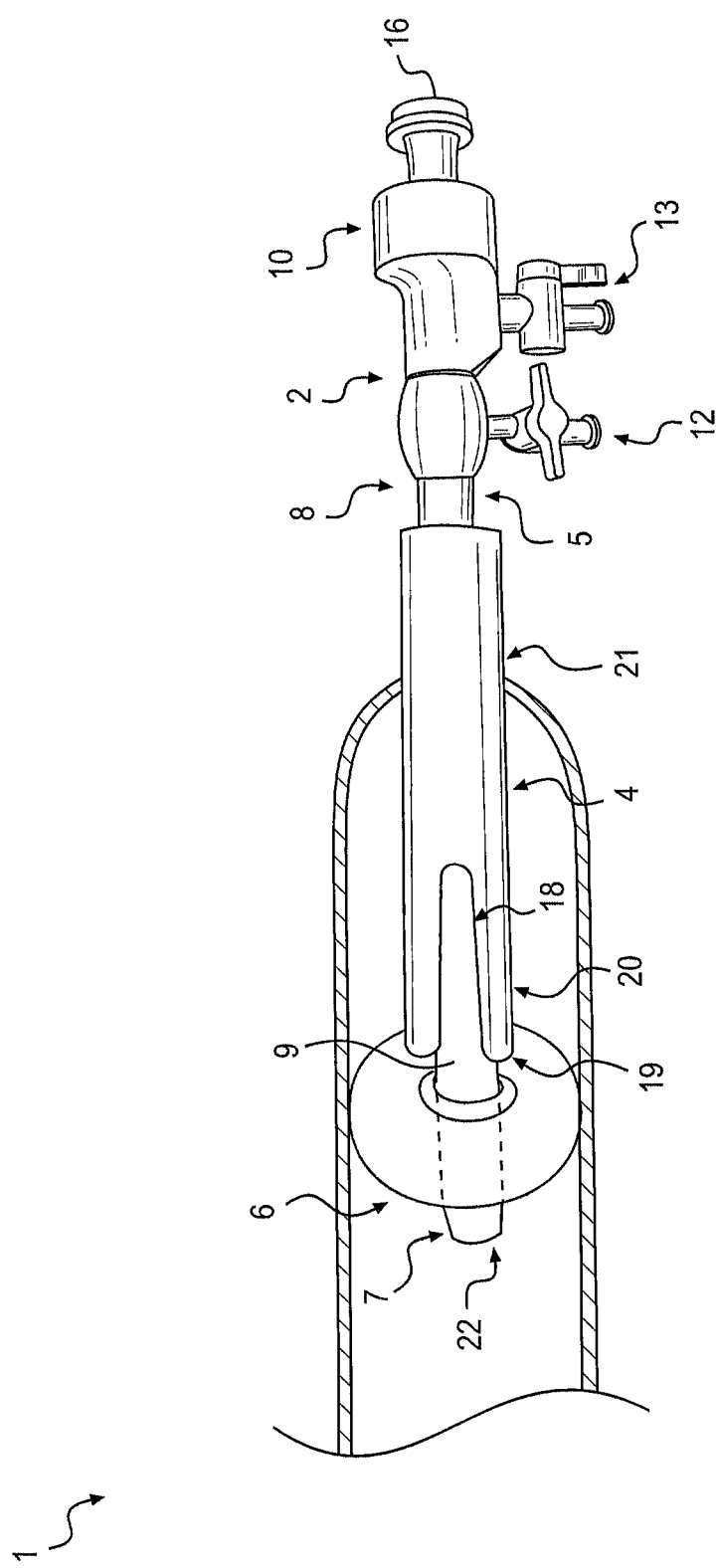
FIG. 9A illustrates an expandable member of a dissection port expanded to separate adjacent tissues layers, according to an exemplary disclosed embodiment.
Figure 9B:
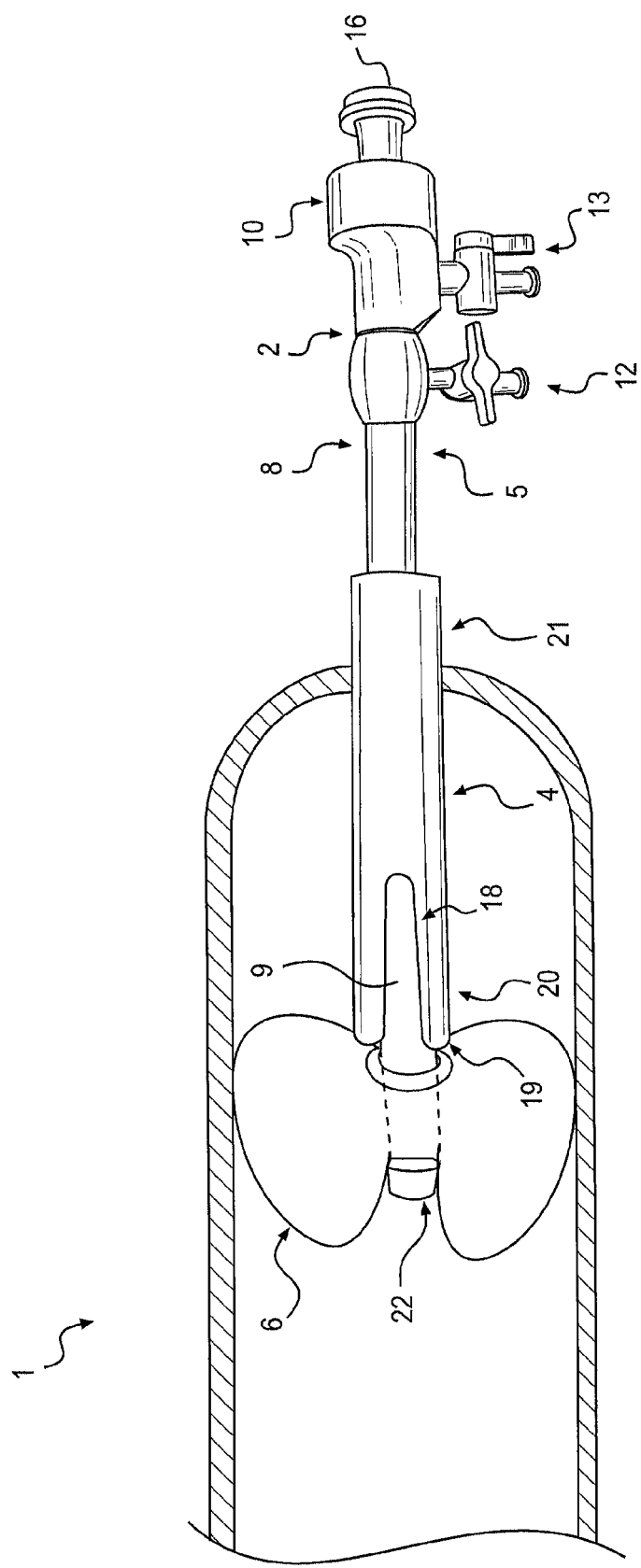
FIG. 9B illustrates an overtube manipulating a configuration of the expandable member of the dissection port of FIG. 9A, according to an exemplary disclosed embodiment.

FIGS. 9A and 9B illustrate another exemplary embodiment of dissection port 1 including port component 2 positioned within overtube 4. In the embodiment of FIGS. 9A and 9B, expandable member 6 may separate adjacent tissues layers, and may be further manipulated by overtube 4.

As shown in FIG. 9A, overtube 4 may first be proximally retracted, or elongate member 5 may be distally advanced, such that an entirety of expandable member 6 may be exposed to the target anatomy surrounding expandable member 6 (e.g., the adjacent tissue layers). Expandable member 6 may then be inflated to its fully-expanded state to separate the tissue layers and form a seal between the tissue layers and expandable member 6.

As shown in FIG. 9B, overtube 4 may be distally advanced and/or port component 2 may be proximally retracted, such that overtube 4 may abut against expandable member 6 and push expandable member 6 in a distal direction relative to elongate member 5. An operator may distally advance expandable member 6 relative to elongate member 5 by pushing on the proximal end of expandable member 6 with overtube 4. A portion of expandable member 6 may be advanced distal to distal face 22 of elongate member 5. Accordingly, expandable member 6 may provide a funnel-like configuration in communication with distal face 22 of elongate member 5. A portion of expandable member 6 may be positioned around a periphery of distal face 22, and may extend distally and in front of distal face 22.

Figure 10A:
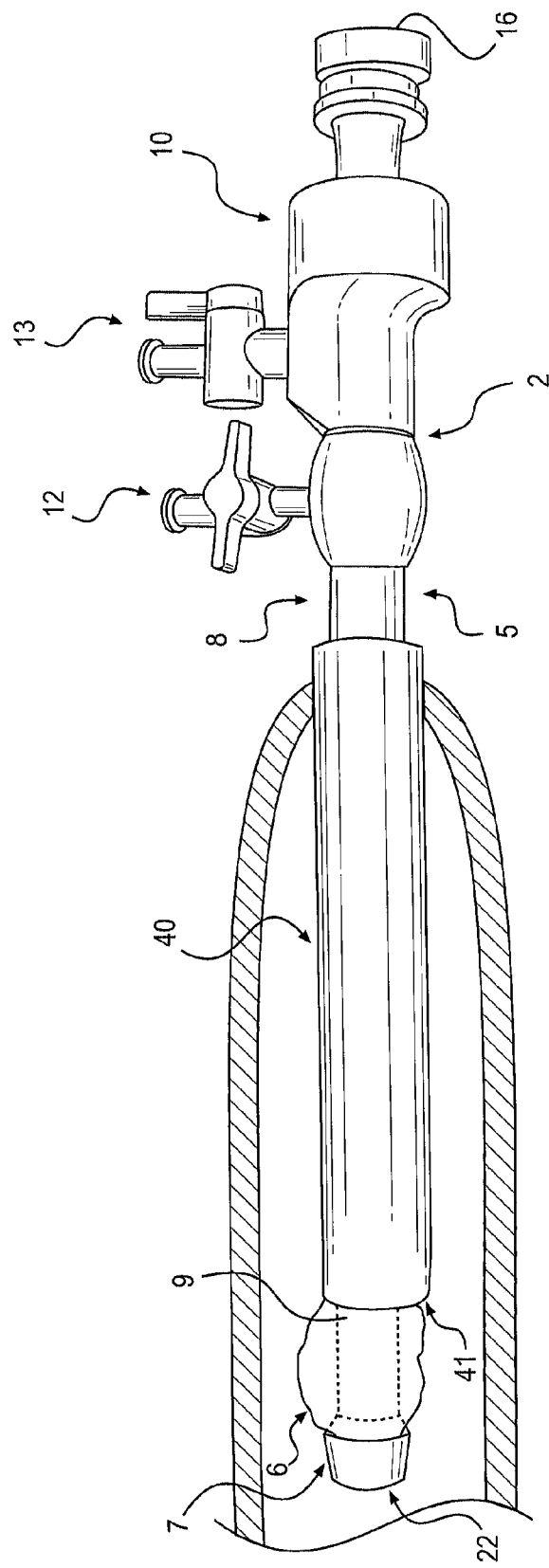
FIG. 10A illustrates an expandable member of a dissection port in a collapsed state, according to an exemplary disclosed embodiment.
Figure 10:
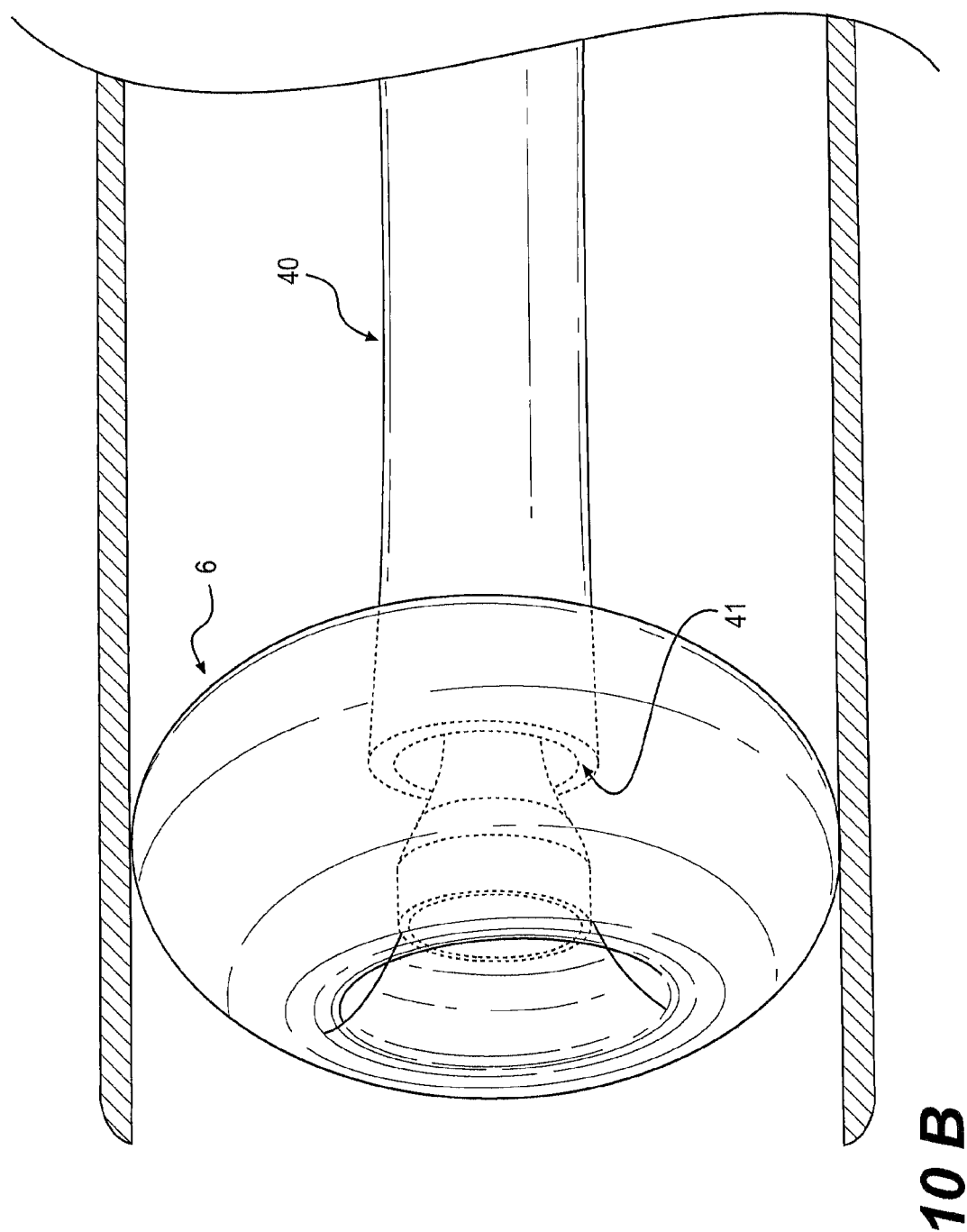
FIG. 10B illustrates an overtube manipulating a configuration of the expandable member of the dissection port of FIG. 10A, as the expandable member is expanded to separate adjacent tissue layers, according to an exemplary disclosed embodiment.

FIGS. 10A and 10B illustrate another exemplary embodiment of expandable member 6 distally advanced relative to elongate member 5. In such an embodiment, an overtube 40 may be employed. Overtube 40 may include a distal face 41 and a lumen extending between distal face 41 and a proximal end of overtube 40. Moreover, the lumen of overtube 40 may be completely surrounded by the walls of overtube at distal face 41.

As shown in FIG. 10A, overtube 40 first may be appropriately positioned over expandable member 6 in its collapsed state. For example, overtube 40 may be positioned over expandable member 6 such that a portion of expandable member 6 may be housed within overtube 40. Distal face 41 of overtube 40 may be positioned between the proximal end and the distal end of expandable member 6.

As shown in FIG. 10B, expandable member 6 may then be inflated, and overtube 40 may be maintained at its position relative to expandable member 6. Accordingly, upon inflation of expandable member 6, overtube 40 may distally direct a portion of expandable member 6 out of distal face 41, and the portion of expandable member 6 that exits distal face 41 may abut against the walls of overtube 40 defining distal face 41. As expandable member 6 is further inflated, the walls of distal face 41 may push against the portion of expandable member 6 that exits distal face 41, and that portion of expandable member 6 may stretch and extend distally away from overtube 40. Similar to the embodiment of FIGS. 9A and 9B, the portion of expandable member 6 external overtube 40 may be positioned around a periphery of distal face 22 of elongate member 5. It should also be appreciated that overtube 40 may also include one or more similar displacement slots as overtube 4 discussed above.

The embodiments of FIGS. 9A-10B may, for example, allow tissue facing distal face 22 of elongate member 5 to be pushed away from dissection port 1 for any suitable procedure. For example, distally extending a portion of expandable member 6 may push away tissue facing distal face 22 of expandable member 6 to provide a suitable amount of space between distal face 22 and the tissue for, as examples, visualization and treatment purposes. In addition, distally extending a portion of expandable member 6 in front of distal face 22 may protect certain tissue from trauma and/or disruption caused by contact with distal face 22 or, for example, by limiting the volume of expandable member 6.

Figure 11A:
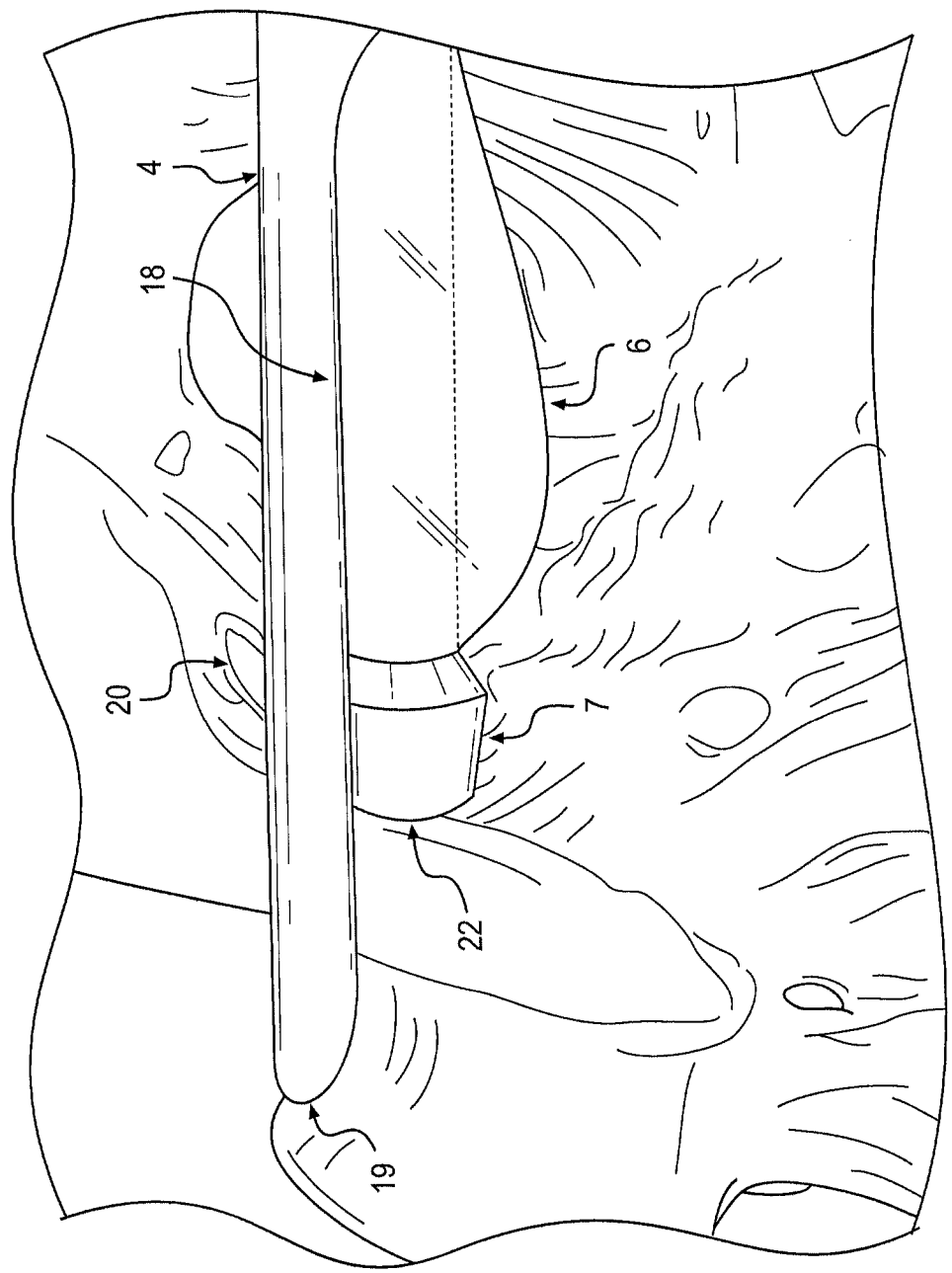
FIG. 11A illustrates a perspective view of an overtube of a dissection port contacting an anatomical landmark, according to an exemplary disclosed embodiment.
Figure 11B:
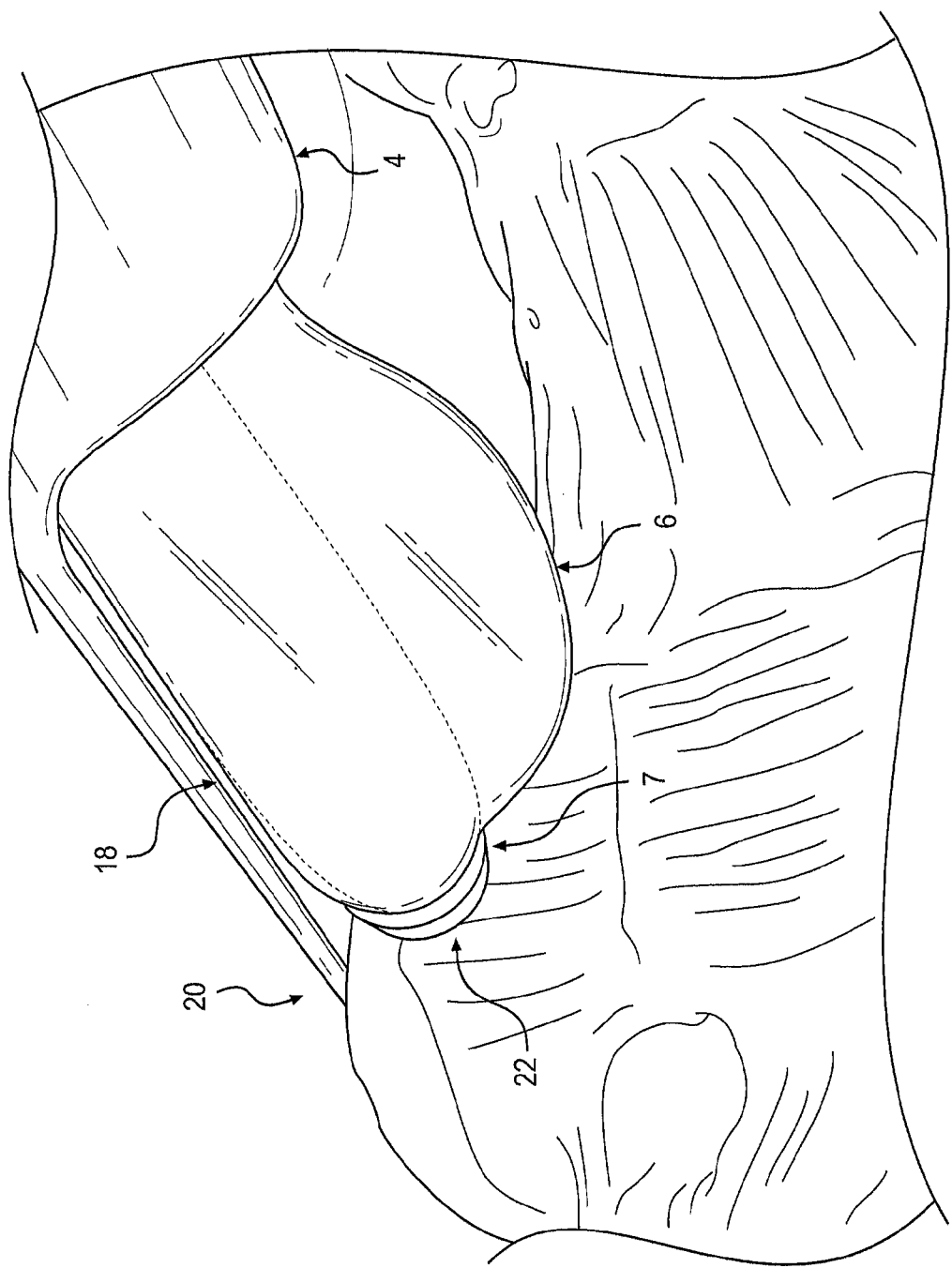
FIG. 11B illustrates another perspective view of an overtube of a dissection port contacting an anatomical landmark, according to an exemplary disclosed embodiment.

FIGS. 11A and 11B illustrate an exemplary embodiment of overtube 4 in use as a guide for dissection port 1. As shown in FIGS. 11A and 11B, overtube 4 may be manipulated by the operator to position and support dissection port 1 relative to a target area. For example, distal portion 20 of overtube 4 may be utilized as a probe to locate certain anatomical landmarks, such as, for example, tissue, bone, ligaments, and the like. The operator may distally advance and proximally retract overtube 4 until overtube 4 contacts the targeted anatomical landmark. Such manipulation may be performed in conjunction with an optical device. In addition, overtube 4 may be employed as a support structure for dissection port 1 during a desired procedure. For instance, and as shown in FIGS. 11A and 11B, distal portion 20 of overtube 4 may lay on top of the anatomical landmark, such as the sacral promontory, to support and align dissection port 1 relative to target tissue, such as vessels, ligaments, and other tissue associated with the sacrum, pelvis, or vagina. Overtube 4 may be positioned such that slot 18 may face the target tissue. Accordingly, port component 2 may be manipulated by the operator relative to slot 18 to treat the target tissue. For example, as dissection port 1 is aligned and stabilized by placing overtube 4 on top of the sacral promontory, the working instruments and tools of port component 2 may be manipulated by the operator for, as examples, treatment and visualization purposes.

Figure 12A:
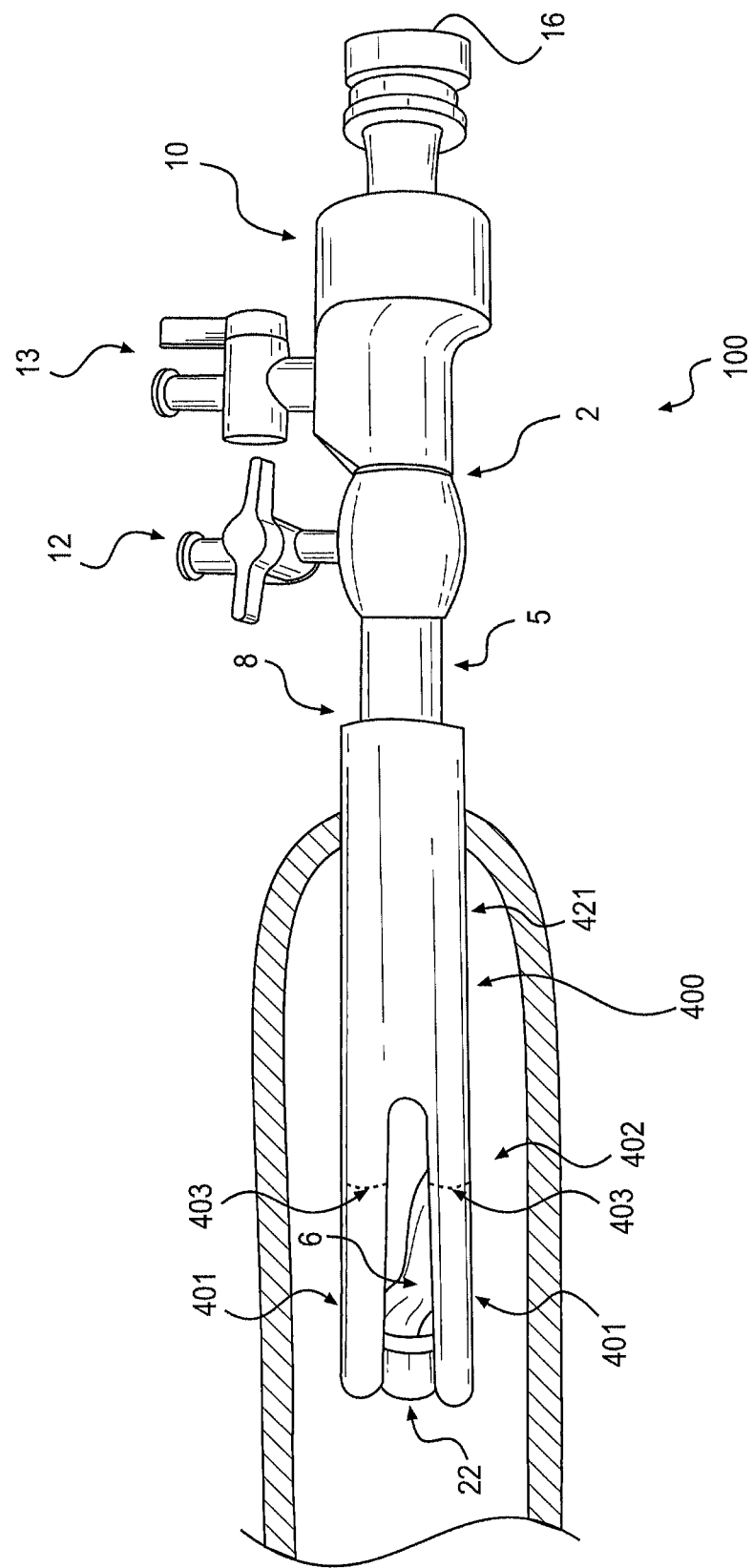
FIG. 12A illustrates a side view of another dissection port, according to an exemplary disclosed embodiment.
Figure 12B:
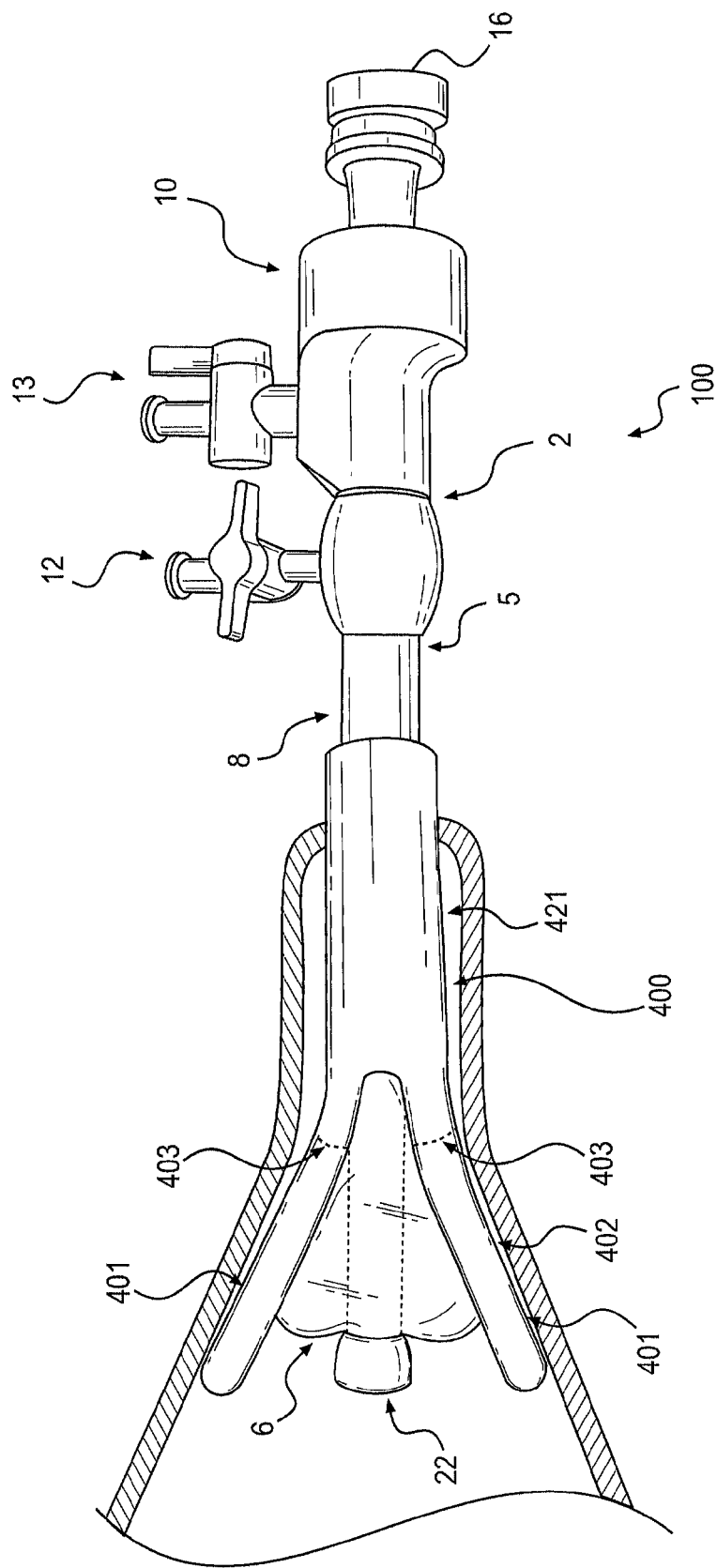
FIG. 12B illustrates a side view of an overtube of the dissection port of FIG. 12A articulated to separate adjacent tissue layers, according to an exemplary disclosed embodiment.

FIGS. 12A and 12B illustrate an exemplary embodiment of another dissection port 100. Similar to the embodiments above, dissection port 100 may include port component 2. In addition, dissection port 100 may include an overtube 400, and port component 2 may be positioned within and configured to move relative to overtube 400. Overtube 400 may include one or more deflectable portions 401 positioned at a distal end 402 of overtube 400. One or more deflectable portions 401 may be configured to articulate from a collapsed position (FIG. 12A) to a deflected position (FIG. 12B).

As shown in FIG. 12A, when overtube 400 is in the collapsed position, one or more deflectable portions 401 may be substantially aligned with a proximal portion 421 of overtube 400. That is, an angle between each deflectable portion 401 and proximal portion 421 may be substantially 180°. Accordingly, with overtube 400 in the collapsed position, dissection port 100 may be delivered through smaller and more restrictive anatomical cavities, and expandable member 6 and cannula 9 may be substantially protected from contact with its external environment.

As show in FIG. 12B, when overtube 400 is in the deflected position, one or more deflectable portions 401 may be laterally deflected relative to a longitudinal axis of overtube 400. In other words, an angle between each deflectable portion 401 and proximal portion 421 may be less than 180°. Deflectable portions 401 may be configured to rotate, or deflect, around pivots 403. Pivots 403 may include any suitable structure configured to effectuate relative movement between deflectable portions 401 and proximal portion 421. For example, each pivot 403 may include a suitable hinge. In some embodiments, deflectable portions 401 and proximal portion 421 may be a single piece of material, and pivots 403 may include a dent or a score between deflectable portions 401 and proximal portion 421. Additionally, or alternatively, the single piece of material may be an elastic material, and deflectable portions 401 may resiliently bend at pivots 403.

Referring back to FIG. 12A, overtube 400 may transition from the collapsed position to the deflected position by first placing expandable member 6 of port component 2 laterally adjacent to one or more deflectable portions 401. In other words, expandable member 6 may be positioned under (or above) one or more deflectable portions 401. In FIG. 12A, expandable member 6 is positioned between portions 401, within overtube 400.

As shown in FIG. 12B, inflation fluid may then be delivered to expand expandable member 6, and consequently, expandable member 6 may push against one or more deflectable portions 401 and laterally move one or more deflectable portions 401 relative to the longitudinal axis of overtube 400. In certain embodiments, overtube 400 may transition from the collapsed positioned to the deflected position without expanding expandable member 6. Overtube 400 may include one or more control members, such as, for example, control wires, rods, or tubes, coupled to one or more deflectable portions 401. The operator may then proximally retract the control members to deflect one or more deflectable portions 401 relative to proximal portion 421. Deflectable portions 401 may have any useful shape or design for the particular procedure. They may be fingers, pedal-like, split tube, curved or bent, and so forth. They may be reinforced to assist in the movement of tissue and organs. If there are more than one, any of the portions 401 may be identical or different with respect to other such portions 401; especially based on treatment or anatomical location.

By deflecting deflectable portions 401, anatomical material, such as, for example, tissue layers, organs, ligaments, and the like, surrounding overtube 400 may be pushed away from dissection port 100. As such, port component 2 may be able to separate tissue layers and/or reach and treat a target region without restriction and interference from the anatomical material pushed away by deflectable portions 401. For example, the target region may be visualized by port component 2, as well as treated by the working instruments and tools delivered through port component 2, with a clear path to the target region.

Overtube 400 may transition back from the deflected position to the collapsed position by deflating expandable member 6 (FIG. 12A). In such embodiments, deflectable portions 401 may be suitably biased to return to the collapsed position. For example, a spring may be suitably positioned at pivot 403 to bias deflectable portions 401 in the collapsed position, or deflectable portions 401 may be formed of a suitable elastic material configured to bias deflectable portions 401 to the collapsed position.

In embodiments where overtube 400 may include one or more control members, the operator may distally advance the control members to return deflectable portions 401 to the collapsed position. Alternatively, deflectable portions 401 may be suitably biased in the collapsed position, and the operator may merely release the proximal force on the control members to return deflectable portions 401 to the collapsed position.

It should be appreciated that overtube 400 may include a suitable locking mechanism configured to hold deflectable portions 401 in any suitable position. For example, the locking mechanism may secure deflectable portions 401 in the deflected position, and may release deflectable portions 401 from the deflected position when desired. As an example, a suitable holding apparatus may be configured to lock the position of the control members, and thus, the position of deflectable portions 401. Furthermore, overtube 400 may include any suitable stops or limiters to restrict the deflection of deflectable portions 401. Such stops or limiters may be symmetrical or asymmetrical. In other words, such stops or limiters may allow deflectable portions 401 to deflect the same distance/angle or different distances/angles relative to each other. In addition, although the embodiment of FIGS. 12A and 12B illustrate two deflectable portions 401, it should be appreciated that overtube 400 may include one deflectable portion 401 or more than two deflectable portions 401.

For any of the embodiments discussed above, it should be appreciated that dissection port 1, 100 may include a suitable locking mechanism to lock the longitudinal position and/or the radial position of overtube 4, 400 relative to port component 2. For example, the locking mechanism may secure the longitudinal position and/or the radial position of overtube 4 such that slot 18 may substantially face expandable member 6, and such that overtube 4 may be fixed from movement when expandable member 6 is expanded. In addition, the locking mechanism may secure the longitudinal position of overtube 400 such that deflectable portions 401 may be laterally adjacent to expandable member 6, and such that overtube 400 may be fixed from movement when expandable member 6 is expanded.

Dissection port 1, 100 may provide the ability for the operator to selectively control a direction, a volume, and/or a position of expandable member 6 in its expanded configuration. For example, radial expansion of expandable member 6 may be manipulated by moving slot 18 of overtube 4 to desired radial and longitudinal positions relative to elongate member 5. In addition, longitudinal expansion of expandable member 6 may be manipulated by adjusting a longitudinal position of overtube 4, 400 relative to expandable member 6. Accordingly, the operator may selectively separate or push away anatomical targets, such as tissue layers, from dissection port 2 by manipulating overtube 4, 400 and directing the expansion of expandable member 6. Furthermore, overtube 4, 400 may selectively block certain portions of expandable member 6 from expanding and contacting anatomical targets. Thus, desired anatomical targets may be separated from and/or dissected by dissection port 1, 100, while disruption of adjacent anatomical targets may be prevented.

Dissection port 1, 100 may also provide the ability to perform multiple tasks without having to remove port component 2 from inside the patient. For example, expandable member 6 of dissection port 1, 100 may dissect tissue and provide a seal between dissection port 1, 100 and the tissue of the patient without having to remove elongate member 5 or port component 2 from inside the patient and without having to use any additional expandable members. Furthermore, while maintaining the seal and without having to remove port component 2 from the patient, insert component 3 may be replaced with a different insert component, e.g., to provide a different configuration of lumens based on the intended tasks to be performed and the working instruments to be used, and/or the working instruments may be replaced with different working instruments. Moreover, while maintaining the seal and without having to remove port component 2 from the patient, expandable member 6, insert component 3, and/or the working instruments may be used to retract, move, or push/pull against tissue or body organs inside the patient with or without insufflating the working space WS. Expandable member 6 in its expanded configuration, when positioned between two dissected tissue layers, may not only anchor elongate member 5 and port component 2 to the patient but may also retract the dissected tissue layers by a desired amount.

Furthermore, port component 2 may remain in the body while the functions (e.g., dissection, sealing, and/or anchoring) of dissection port 1, 100 are performed. Insert component 3 may simply be removed and replaced to support the various functions and tasks of dissection port 1, 100. Accordingly, the position of port component 2 inside the patient may be maintained, resulting in less trauma to the patient and fewer complications.

Any aspect set forth in any embodiment may be used with any other embodiment set forth herein. Every device and apparatus set forth herein may be used in any suitable medical procedure, may be advanced through any suitable body lumen and body cavity, and may be used to access tissue from any suitable body portion. For example, the apparatuses and methods described herein may be used through any natural body lumen or tract, including those accessed orally, vaginally, rectally, nasally, urethrally, or through incisions in any suitable tissue.

It will be apparent to those skilled in the art that various modifications and variations can be made in the disclosed systems and processes without departing from the scope of the invention. For example, the dissection port 1, 100 may include a vibrator for vibrating one or more components of the dissection port 1, 100. Such a vibrator may provide vibrations in the transverse and/or the longitudinal directions. The vibrator may include an electric motor, a solenoid, and/or other electric devices coupled to, for example, housing 10 of dissection port 1, 100. In addition, the vibrator may be configured to pulse fluid conveyed through the dissection port 1, 100. The vibrator vibrating the fluid and/or the dissection port 1, 100 itself, may assist in separating layers of tissue as the dissection port 1, 100 advances.

Other embodiments of the invention will be apparent to those skilled in the art from consideration of the specification and practice of the invention disclosed herein. It is intended that the specification and examples be considered as exemplary only. The following disclosure identifies some other exemplary embodiments.

What is claimed is:

1. A medical device for providing access within a patient, comprising:
   an overtube having a lumen and a slot defined by a side-surface of the overtube, the slot having a length less than a length of the overtube; and
   an elongate member configured to be disposed within the lumen of the overtube, the elongate member defining a bore that extends a length of the elongate member, the elongate member including an expandable member at a distal end portion of the elongate member and configured to expand and collapse, the overtube configured to move longitudinally relative to the elongate member between a plurality of positions including a first position and a second position;
   wherein, upon expansion of the expandable member when the overtube is in the first position, a first portion of the expandable member facing the slot is configured to expand out of the slot, and a second portion of the expandable member facing away from the slot is restricted from expansion by the overtube, wherein the overtube is configured to move distally to the second position such that a volume of the first portion expanded through the slot is decreased;
   an insert component configured to be inserted into the bore of the elongate member; and
   a first valve disposed on a housing of the elongate member, the first valve fluidly coupled to the bore of the elongate member, wherein the first valve is configured to permit passage of insufflation fluid through the bore and out of the elongate member in order to dissect tissue layers.

2. The medical device of claim 1, wherein the overtube is configured to radially move relative to the elongate member to manipulate a position of the slot around the expandable member.

3. The medical device of claim 1, wherein the overtube includes a distal face having a substantially arcuate cross-sectional shape.

4. The medical device of claim 1, wherein the slot extends through a distal face of the overtube.

5. The medical device of claim 1, wherein the overtube is configured to retract proximally to a third position such that no portion of the expandable member is restricted from expansion by the overtube.

6. The medical device of claim 5, wherein, when the overtube is in the third position, the expandable member is configured to expand around a circumference of the elongate member at the distal end portion of the elongate member.

7. The medical device of claim 1, wherein the elongate member also defines an inflation lumen fluidly coupled to the expandable member, the medical device further comprising:
   a second valve disposed on the housing of the elongate member, the second valve fluidly coupled to the inflation lumen, wherein the second valve is configured to permit fluid to enter the inflation lumen to expand the expandable member, and to vent fluid inside the expandable member to collapse the expandable member.

8. The medical device of claim 1, wherein the expandable member is an elastic balloon-shaped structure.

9. The medical device of claim 1, wherein the elongate member defines a first opening of the bore at a distal end of the elongate member, and a second opening of the bore at a proximal end of the elongate member, wherein the insert component is configured to be inserted into the bore of the elongate member at the second opening.

10. The medical device of claim 9, wherein the insert component includes a flange at a proximal end of the insert component, wherein, when the insert component is inserted into the bore, the flange abuts the proximal end of the elongate member, and a distal end of the insert component extends out of the first opening.

11. The medical device of claim 1, wherein the slot includes a distal end and a proximal end, the distal end of the slot being disposed a distance away from a distal face of the overtube.

12. The medical device of claim 1, wherein the slot includes a distal end and a proximal end, the distal end of the slot extending to a distal face of the overtube.

13. A medical device for providing access within a patient, comprising:
    an overtube having a lumen and a slot defined by a side-surface of the overtube, the slot having a length less than a length of the overtube, the slot extending through a distal end face of the overtube:
    an elongate member configured to be disposed within the lumen of the overtube, the elongate member including an expandable member at a distal end portion of the elongate member and configured to expand and collapse,
    the overtube configured to move longitudinally relative to the elongate member between a plurality of positions including a first position and a second position, the elongate member defining an inflation lumen fluidly coupled to the expandable member, the elongate member also defining a bore extending through a length of the elongate member; and
    an insert component configured to be inserted into the bore of the member,
    wherein, upon expansion of the expandable member when the overtube is in the first position, a first portion of the expandable member facing the slot is configured to expand out of the slot, and a second portion of the expandable member facing away from the slot is restricted from expansion by the overtube.

14. The medical device of claim 13, wherein, when the overtube is retract proximally to the second position, no portion of the expandable member is restricted from expansion by the overtube.

15. The medical device of claim 13, further comprising:
- a first valve disposed on a housing of the elongate member, the first valve fluidly coupled to the inflation lumen, wherein the first valve is configured to permit fluid to enter the inflation lumen to expand the expandable member, and to vent fluid inside the expandable member to collapse the expandable member; and
- a second valve disposed on the housing of the elongate member, the second valve fluidly coupled to the bore of the elongate member, wherein the second valve is configured to permit passage of insufflation fluid through the bore and out of a distal end of the elongate member.

16. The medical device of claim 15, wherein the insert component includes a flange at a proximal end of the insert component, wherein, when the insert component is inserted into the bore, the flange abuts a proximal end of the elongate member.

\* \* \* \* \*